(12) United States Patent
Mundschau et al.

(10) Patent No.: US 11,234,905 B2
(45) Date of Patent: *Feb. 1, 2022

(54) FORMULATIONS HAVING IMPROVED COMPATIBILITY WITH NONWOVEN SUBSTRATES

(75) Inventors: Stacy Averic Mundschau, Weyauwega, WI (US); Scott W. Wenzel, Neenah, WI (US); Lisa Ann Flugge-Berendes, Appleton, WI (US); Debra Hartley Durrance, Appleton, WI (US); Jonathan Kyle Arendt, New London, WI (US); Kroy Donald Johnson, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 991 days.

This patent is subject to a terminal disclaimer.

(21) Appl. No.: 12/172,039

(22) Filed: Jul. 11, 2008

(65) Prior Publication Data

US 2010/0008957 A1 Jan. 14, 2010

(51) Int. Cl.

| A01N 43/00 | (2006.01) |
|---|---|
| A01N 43/46 | (2006.01) |
| A61K 31/55 | (2006.01) |
| A61K 8/02 | (2006.01) |
| A61K 8/891 | (2006.01) |
| A61K 8/37 | (2006.01) |
| A61Q 19/00 | (2006.01) |

(52) U.S. Cl.
CPC .............. *A61K 8/0208* (2013.01); *A61K 8/37* (2013.01); *A61K 8/891* (2013.01); *A61Q 19/00* (2013.01)

(58) Field of Classification Search
None
See application file for complete search history.

(56) References Cited

U.S. PATENT DOCUMENTS

| 3,301,746 A | 1/1967 | Sanford et al. |
|---|---|---|
| 3,338,992 A | 8/1967 | Kinney |
| 3,341,394 A | 9/1967 | Kinney |
| 3,473,576 A | 10/1969 | Amneus |
| 3,502,763 A | 3/1970 | Hartmann |
| 3,542,615 A | 11/1970 | Dobo et al. |
| 3,573,164 A | 3/1971 | Friedberg et al. |
| 3,675,121 A | 7/1972 | Thompson |
| 3,692,618 A | 9/1972 | Dorschner et al. |
| 3,802,817 A | 4/1974 | Matsuki et al. |
| 3,812,000 A | 5/1974 | Salvucci, Jr. et al. |
| 3,821,068 A | 6/1974 | Shaw |
| 3,849,241 A | 11/1974 | Butin et al. |
| 3,896,807 A | 7/1975 | Buchalter |
| 3,974,025 A | 8/1976 | Ayers |
| 4,011,389 A | 3/1977 | Langdon |
| 4,134,838 A | 1/1979 | Hooper et al. |
| 4,137,180 A | 1/1979 | Naik et al. |
| 4,191,609 A | 3/1980 | Trokhan |
| 4,208,459 A | 6/1980 | Becker et al. |
| 4,239,065 A | 12/1980 | Trokhan |
| 4,340,563 A | 7/1982 | Appel et al. |
| 4,347,931 A | 9/1982 | Ginger et al. |
| 4,528,239 A | 7/1985 | Trokhan |
| 4,637,859 A | 1/1987 | Trokhan |
| 4,720,415 A | 1/1988 | Vander Wielen et al. |
| 4,767,547 A | 8/1988 | Straathof et al. |
| 4,788,733 A | 12/1988 | Lerner |
| 4,789,491 A | 12/1988 | Chang et al. |
| 4,812,284 A | 3/1989 | Fleissner |
| 5,169,251 A | 12/1992 | Davis |
| 5,213,881 A | 5/1993 | Timmons et al. |
| 5,364,382 A | 11/1994 | Latimer et al. |
| 5,486,166 A | 1/1996 | Bishop et al. |
| 5,490,846 A | 2/1996 | Ellis et al. |
| 5,539,056 A | 7/1996 | Yang et al. |
| 5,596,052 A | 1/1997 | Resconi et al. |
| 5,607,551 A | 3/1997 | Farrington, Jr. et al. |
| 5,614,202 A | 3/1997 | DeFina |
| 5,639,532 A | 6/1997 | Wells |
| 5,690,918 A | 11/1997 | Jacks et al. |
| 5,869,072 A | 2/1999 | Berry |
| 6,013,270 A | 1/2000 | Hargraves et al. |
| 6,037,281 A | 3/2000 | Mathis et al. |

(Continued)

FOREIGN PATENT DOCUMENTS

| EP | 0032793 A2 | 7/1981 |
|---|---|---|
| EP | 0147146 A2 | 7/1985 |

(Continued)

OTHER PUBLICATIONS

Kamath, et al., "Finishing of Nonwoven Bonded Fabrics," http://web.utk.edu/~mse/Textiles/Finishing%20of%20Nonwovens.htm, updated Apr. 2004, printed Aug. 5, 2008 (11 pages).

"Materials Science & Engineering 554, Nonwovens Science and Technology II," http://web.utk.edu/~mse/Textiles/index.html, Spring 2004, printed Aug. 5, 2008 (2 pages).

Gao, et al., "Thermal Bonding of Nonwoven Fabrics," Educational Research Nonwoven Thermal Bonding, http://www.apparelsearch.com/Education/Research/Nonwoven/2001_Kermit_Duckett/education_research_nonwoven_thermal_bonding.htm, 2001, printed Aug. 4, 2008 (10 pages).

Quack, R., et al., "Calender Processes in the Nonwoven Industry," International Nonwovens Technical Conference, INTC 2001, Sep. 5-7, 2001, 15p.

Scruggs, J., "A brief overview of the evolution of propylene fiber processes," Propylene Technology Conference, Aug. 31-Sep. 1, 1994, 10 p.

(Continued)

*Primary Examiner* — Layla Soroush
(74) *Attorney, Agent, or Firm* — Armstrong Teasdale LLP

(57) ABSTRACT

Nonwoven and elastomeric substrates having formulations disposed thereon, wherein the formulations have improved compatibility with the substrate, are disclosed herein. More particularly, the formulations can be applied on the substrates without compromising the elastomeric properties and overall integrity of the substrate. Laminated articles using one or more of the nonwoven and elastomeric substrates having the formulations disposed thereon are further disclosed.

11 Claims, 3 Drawing Sheets

(56) References Cited

U.S. PATENT DOCUMENTS

| | | | |
|---|---|---|---|
| 6,180,584 | B1 | 1/2001 | Sawan et al. |
| 6,261,580 | B1 | 7/2001 | Lehrter et al. |
| 6,274,154 | B1 | 8/2001 | Chou |
| 6,383,999 | B1 | 5/2002 | Coyle et al. |
| 6,423,328 | B2 | 7/2002 | Chou |
| 6,500,443 | B1 | 12/2002 | Otts et al. |
| 6,500,563 | B1 | 12/2002 | Datta et al. |
| 6,513,998 | B1 | 2/2003 | Barry |
| 6,630,152 | B2 | 10/2003 | Chou |
| 6,638,587 | B1 | 10/2003 | Wang et al. |
| 6,896,766 | B2 | 5/2005 | Sarbo et al. |
| 6,953,582 | B2 | 10/2005 | Chou |
| 6,958,103 | B2 | 10/2005 | Anderson et al. |
| 6,960,349 | B2 | 11/2005 | Shantz et al. |
| 7,147,752 | B2 | 12/2006 | Shannon et al. |
| 2002/0006886 | A1 | 1/2002 | Beerse et al. |
| 2003/0228351 | A1 | 12/2003 | Hasenochrl et al. |
| 2004/0115250 | A1 | 6/2004 | Loo et al. |
| 2004/0122382 | A1 | 6/2004 | Johnson et al. |
| 2004/0126604 | A1 | 7/2004 | Wang et al. |
| 2004/0241201 | A1* | 12/2004 | Wang et al. ............ 424/401 |
| 2005/0079192 | A1 | 4/2005 | Simon |
| 2005/0081278 | A1 | 4/2005 | Williams et al. |
| 2005/0106201 | A1 | 5/2005 | Janssen |
| 2005/0222543 | A1 | 10/2005 | Shao |
| 2005/0260147 | A1* | 11/2005 | Elliott et al. ............ 424/63 |
| 2006/0008621 | A1 | 1/2006 | Gusky et al. |
| 2006/0070167 | A1 | 4/2006 | Eng et al. |
| 2006/0074029 | A1 | 4/2006 | Leece |
| 2006/0143767 | A1* | 7/2006 | Yang et al. ............ 2/16 |
| 2007/0244203 | A1 | 10/2007 | Raul et al. |
| 2007/0259029 | A1 | 11/2007 | McEntire et al. |

FOREIGN PATENT DOCUMENTS

| | | | |
|---|---|---|---|
| EP | 0591609 | A1 | 4/1994 |
| EP | 0617164 | A1 | 9/1994 |
| EP | 0677612 | A2 | 10/1995 |
| EP | 1088540 | | 4/2001 |
| EP | 1088540 | A1 | 4/2001 |
| EP | 1125540 | A1 | 8/2001 |
| EP | 1266600 | A1 | 12/2002 |
| EP | 1444970 | A1 | 8/2004 |
| EP | 1454577 | A2 | 9/2004 |
| FR | 2813777 | A1 | 3/2002 |
| WO | 2003022962 | A2 | 3/2003 |
| WO | 03075879 | A2 | 9/2003 |
| WO | 2003105916 | A1 | 12/2003 |
| WO | 2004043179 | A2 | 5/2004 |
| WO | 2004043235 | A2 | 5/2004 |
| WO | 2004060432 | A1 | 7/2004 |
| WO | 2004108036 | A1 | 12/2004 |
| WO | 2006110271 | | 10/2006 |
| WO | 2007018822 | A1 | 2/2007 |
| WO | 2007064343 | A2 | 6/2007 |

OTHER PUBLICATIONS

Smith, P., "Nonwoven Fabric Machinery," Textile Hroizons, Feb./Mar. 1992, vol. 12, Issue 2, p. 34-35.

Reddy, et al., "Stability Testing of O/W Emulsions Through Dielectric Constant—I," Cosmetics & Toiletries, vol. 99 (10), Oct. 1984, p. 67-72.

International Search Report and Written Opinion of PCT/IB2009/052989 dated Feb. 26, 2010.

Product information for ABIL WE 09; EVONIK Industries, 2008.

International Search Report and Written Opinion of International Application No. PCT/IB2009/052990, dated Mar. 2, 2010.

Non-final Office Action regarding U.S. Appl. No. 12/022,328, dated Jun. 28, 2011.

Final Office Action regarding U.S. Appl. No. 12/022,328, dated Dec. 6, 2011.

Non-final Office Action regarding U.S. Appl. No. 12/172,049, dated Dec. 23, 2010.

Final Office Action regarding U.S. Appl. No. 12/172,049, dated Jun. 9, 2011.

Office Action for Russian Application No. 2011104725/15 dated Nov. 23, 2012; 6 pages.

Office Action for Russian Application No. 2011104727/15 dated Dec. 14, 2012; 4 pages.

Lewis, Sr. Richard J., "Hawley's Condensed Chemical Dictionary," Wiley-Interscience, p. 854 (2007).

Office action issued for U.S. Appl. No. 12/022,328 (dated Dec. 19, 2013).

Supplementary European Search Report for EP Application Serial No. 09794090 dated Apr. 8, 2013.

European Search Report for U.S. Appl. No. 09/794,091 dated Jul. 4, 2013; 6 pages.

Patent Examination Report No. 1 for Patent Application No. 2009269612 dated Aug. 20, 2013; 5 pages.

* cited by examiner

FORMULATIONS HAVING IMPROVED COMPATIBILITY WITH NONWOVEN SUBSTRATES

BACKGROUND OF THE DISCLOSURE

The present disclosure relates generally to nonwoven and elastomeric substrates having formulations disposed thereon, wherein the formulations have improved compatibility with the substrates. More particularly, the formulations can be applied on the substrates without compromising the elastomeric properties and overall integrity of the substrate. In one embodiment, the formulation has an overall dielectric constant of less than 40.0 and the substrate retains at least about 40% of the tension of the untreated substrate at a target elongation as defined herein.

Consumers have conventionally relied upon various kinds of formulations or compositions for health and/or hygiene benefits. To deliver these benefits, a wide variety of chemistries are often used within a single formulation. One of the more prevalent delivery forms emulsions such as lotions and creams, are particularly useful as they combine high levels of both water and oily substances to deposit on the skin. More particularly, lotions include skin benefit components such as humectants, occlusive agents, emollients, and emulsifiers.

Humectants are hygroscopic agents that are typically used as moisturizers. Furthermore, occlusive agents help improve the overall moisture content of the skin by retarding the evaporation of water from the skin's surface. By blocking the evaporative loss of water, occlusive agents increase the water content of skin.

Lotions additionally rely on emollients to lubricate, soothe, and soften the skin surface. Emollients are generally oily or waxy ingredients that have a major impact on the aesthetics of the finished formulations and on the separation of the water and oil within a lotion emulsion. They also significantly influence the spreading characteristics and overall skin feel of the lotion.

One major problem with conventionally used components in lotion formulations is that the oily substances typically compromise the elastomeric properties and overall integrity of the nonwoven webs used to apply the lotions. More particularly, the lotions can interfere with the mechanical properties of the substrates causing the substrates to lose strength necessary to properly function and even fall apart. Alternatively, the lotions can cause the substrates to be stiff and inflexible, causing a rough feel when used on the consumer's skin.

Furthermore, the lotion formulations are used with nonwoven and elastomeric substrates in laminated substrates that can be donned and conformed to the surface of the consumer's skin. For example, many of these lotions can be applied to the inner layers of gloves or socks to be donned, thereby holding the lotion formulation in contact with the skin's surface. When used with these types of substrates, the lotion formulations can cause delamination of the layers or compromise the web integrity as the oily substances in the lotions interfere with the elastomeric properties. In the end, this incompatibility leads to a product that is unstable and which lacks overall aesthetics, functionality, and potential to deliver beneficial ingredients to the consumer's skin.

As such, there is a significant need for formulations including oily substances that can be applied to the surface of nonwoven and elastomeric substrates that will provide desired skin health benefits and have good aesthetics to the user while not interfering with the substrates' mechanical properties or overall fit of the product. Additionally, it would be advantageous if the lotions could be applied to laminated articles such as gloves or socks that can be donned and conformed to the surface of the user's skin to provide health and hygiene benefits.

BRIEF DESCRIPTION OF THE DISCLOSURE

It has been found that formulations can be produced and applied to substrates and articles for improving skin health without compromising the integrity of the substrates. Particularly, these formulations include components that can improve skin feel and overall aesthetics without interfering with the elastomeric properties of the substrate. Particularly preferred substrates for use with the formulation include nonwoven substrates and elastomeric substrates. In one embodiment, the formulation can include at least one cosmetic carrier for improving skin health and hygiene when applied to the skin.

Additionally, the formulation can be applied to the inner surface of a laminated article capable of conforming to the user's skin when donned. In one preferred embodiment, the laminated article is a glove.

Accordingly, the present disclosure is directed to an elastomeric substrate comprising a formulation. The formulation comprises at least one cosmetic carrier and has greater than 5% (by weight formulation) water. The formulation further has a dielectric constant of less than 40.0. The elastomeric substrate retains at least about 40% of the tension of the untreated substrate at 30% elongation.

The present disclosure is further directed to a nonwoven substrate comprising a formulation. The formulation comprises at least one cosmetic carrier and has greater than 5% (by weight formulation) water. The formulation further has a dielectric constant of less than 40.0. The nonwoven substrate retains at least about 40% of the tension of the untreated substrate at 30% elongation.

The present disclosure is further directed to a laminated article comprising a first substrate and a second substrate. At least one of the first and second substrates comprises a formulation. The formulation comprises at least one cosmetic carrier and has greater than 5% (by weight formulation) water. The formulation further has a dielectric constant of less than 40.0. The laminated article retains at least about 40% of the tension of the untreated substrate at 30% elongation.

Other objects and features will be in part apparent and in part pointed out hereinafter.

DETAILED DESCRIPTION OF THE DISCLOSURE

Figure 1:
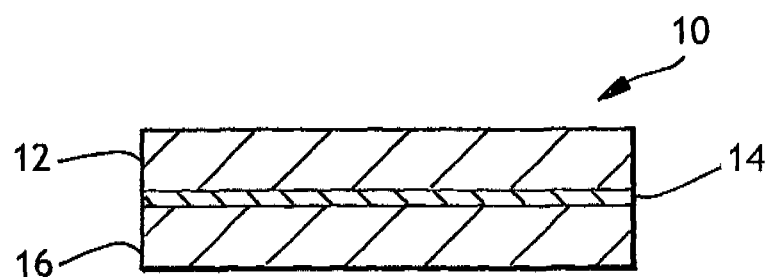
FIG. 1 depicts one embodiment of a laminated article of the present disclosure.

The present disclosure is directed to nonwoven and elastomeric substrates having a formulation deposited thereon for providing skin health and/or hygiene benefits. More particularly, the formulation includes greater than 5% (by weight formulation) water, and preferably, is an emulsion formulation. As the formulation includes water and is not fully dried onto the substrate, the substrate containing the formulation can be made in a single easy processing step as compared to conventional substrates with formulations. This provides for less energy expended due to the lack of drying needed. Further, it has been found that without the need for drying, there are more options for the substrates that can be utilized, better transfer of the formulation from the substrate, allowing for improved skin benefits, such as moisturization to the user, and increased options for the types of skin benefit agents available for use in the formulation.

The formulation further includes at least one cosmetic carrier that can provide one or more skin benefits to the user without interfering with the mechanical properties of the substrate, such as elastomeric properties and/or the overall integrity of the substrate.

Additionally, the present disclosure is directed to laminated articles made from the nonwoven and elastomeric substrates. Particularly, the laminated articles have at least a first outer substrate and a second inner substrate. At least one or both of the first and second substrates may be a nonwoven and/or elastomeric substrates.

Representative Substrates for Use with the Formulations of the Present Disclosure In one embodiment, the substrate for use with the formulations of the present disclosure is an elastomeric substrate. Elastomeric substrates are particularly useful when the substrate is to be used in a laminated article such as a glove or sock, as it is oftentimes desirable for the glove or sock to be able to stretch to provide for easier glove/sock donning. The elastomeric substrate may be formed from a natural or a synthetic latex as well as a dissolved or hot melt extrusion of an elastomeric polymer, such as a thermoplastic elastomeric polyolefin polymer. For instance, the elastomeric substrate may be formed of a natural or synthetic rubber, a nitrile rubber, a nitrile butadiene rubber, a polyisoprene, a polychloroprene, a polyurethane, a neoprene, a homopolymer of a conjugated diene, a copolymer of a least two conjugated dienes, a copolymer of at least one conjugated diene and at least one vinyl monomer, styrene block copolymers, or any other suitable combinations thereof. Examples of suitable synthetic rubbers can also include acrylic diene block copolymers, acrylic rubber, butyl rubber, EPDM rubber, polybutadiene, chlorosulfonated polyethylene rubber, and fluororubber.

The elastomeric substrates (also referred to herein as films) can be formed by mixing the components together, heating and then extruding the components into a monolayer or multi-layer substrate using any one of a variety of elastomeric film-producing processes known to those of ordinary skill in the film processing art. Such film-making processes include, for example, cast embossed, chill and flat cast, and blown film processes.

In one particularly preferred embodiment, the elastomeric substrate is a nonwoven substrate. When a nonwoven substrate is used with the formulation, commercially available thermoplastic polymeric materials can be advantageously employed in making the fibers or filaments from which the substrate is formed. As used herein, the term "polymer" shall include, but is not limited to, homopolymer, copolymers, such as for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random and atactic symmetries. As used herein, the terms "thermoplastic polymer" or "thermoplastic polymer material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, and copolymers thereof.

Alternatively, or in addition to the polymeric materials above, the nonwoven substrates can be prepared from cellulosic fibers. Numerous cellulosic fibers, such as, for example, wood pulp fibers or staple fibers can be used in the nonwoven substrates. Suitable commercially available cellulosic fibers for use in the nonwoven substrates can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

Nonwoven substrates can be formed by a variety of known forming processes, including airlaying, meltblowing, spunbonding, or bonded carded web formation processes. "Airlaid" refers to a porous web formed by dispersing fibers in a moving air stream prior to collecting the fibers on a forming surface. The collected fibers are then typically bonded to one another using, for example, hot air or a spray adhesive. Suitable examples of airlaid webs can be found in U.S. Pat. No. 5,486,166 to Bishop, et al., U.S. Pat. No. 6,960,349, issued to Shantz, et al. (Nov. 1, 2005), and U.S. Publication No. 2006/0008621 to Gusky, et al., all incorporated by reference to the extent that they are consistent herewith.

The fibrous nonwoven substrate material may also comprise meltblown materials. "Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al. Meltblown fibers may be continuous or discontinuous and are generally self bonding when deposited onto a collecting surface.

"Spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the contents of which are incorporated herein by reference in their entirety. Spunbond fibers are generally continuous and have diameters generally greater than about 7 microns, more particularly, between about 10 and about 20 microns.

"Bonded-carded web" refers to a web made from staple fibers sent through a combing or carding unit, which separates or breaks apart and aligns the fibers to form a nonwoven web. The carded fibers are then typically bonded to one another using, for example, hot air or a spray adhesive. The carded fibers are then typically bonded to one another using, for example, hot air or a spray adhesive. For example, the web may be a powder bonded carded web, an infrared bonded carded web, or a through-air bonded carded web. Examples of such materials may be found in U.S. Pat. No. 5,490,846 to Ellis et al.; U.S. Pat. No. 5,364,382 to Latimer; and U.S. Pat. No. 6,958,103 to Anderson, et al.

As noted above, these substrates can be used alone or can be combined to form a laminated article having at least a first substrate and a second substrate. One particularly preferred laminated article of the present disclosure will generally have 3 layers: a water-impermeable substrate, such as a film, sandwiched between two fibrous substrates, such as the nonwoven substrates described above. An example of such a laminated article 10 is depicted in FIG. 1, which representatively illustrates a water-impermeable substrate 14 attached to an outer fibrous substrate 12 and an inner fibrous substrate 16. The material for the outer fibrous substrate 12 may be any nonwoven substrate material described above that provides for a cloth-like appearance (as opposed to, for example, a smooth or rubbery appearance as in neoprene rubber glove). The material for the inner fibrous substrate 16 may be any material that is fibrous in nature, such as the above-described nonwoven substrates. In more preferred embodiments, to ensure optimal elongation and retraction properties, the film described above is comprised of an elastomeric polymer or plurality of elastomeric polymers.

In one embodiment, the inner fibrous substrate should possess an uneven, undulating surface to help contain the formulation applied to the surface of the inner fibrous substrate 16. The undulations (rugosity) of this inner substrate material can be achieved or enhanced by attaching the inner fibrous substrate 16 to the water-impermeable substrate 14 at discrete points or locations (e.g., by thermally point bonding the substrates together, as is discussed in more detail below) while the water-impermeable substrate 14 is in a stretched condition. When the water-impermeable substrate 14 (and, therefore, the resulting laminate article) is allowed to relax, the inner fibrous substrate 16 is gathered to produce undulations in the inner fibrous layer. Of course, both the inner fibrous substrate 16 and the outer fibrous substrate 12 are gathered in this way if they are attached to the water-impermeable substrate 14 at discrete points or locations while the water-impermeable substrate 14 is in a stretched condition (and then allowed to relax).

The inner and outer fibrous nonwoven substrates may be the same or may be different. Generally the water-impermeable substrate 14 is an elastomeric substrate, with the resulting laminated article 10 able to stretch and conform to a hand, foot, extremity, or other body region to which the article is applied.

As noted above, the water-impermeable substrate 14 can be an elastomeric substrate as described above, or can be formed of any other film-type substrate that can be suitably bonded or attached to inner and outer fibrous substrate layers 12 and 16 respectively to yield a laminated article 10 having the performance characteristics and features described herein. In addition to the film-type substrate, the water-impermeable substrate 14 can also include a filler. As used herein, a "filler" is meant to include particulates and other forms of materials which can be added to the film polymer (e.g., elastomeric) extrusion blend and which will not chemically interfere with the extruded film but which are able to be uniformly dispersed throughout the film. Generally, the fillers will be in particulate form and may have a spherical or non-spherical shape with average particle sizes in the range of about 0.1 to about 7 microns. Both organic and inorganic fillers are contemplated to be within the scope of the present disclosure provided that they do not interfere with the film formation process, or the ability of the film layer to function in accordance with the teachings of the present disclosure. Examples of suitable fillers include calcium carbonate ($CaCO_3$), various kinds of clay, silica ($SiO_2$), alumina, barium carbonate, sodium carbonate, magnesium carbonate, talc, barium sulfate, magnesium sulfate, aluminum sulfate, titanium dioxide ($TiO_2$), zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as, for example, stearic acid, may also be applied to the filler particles.

Other additives may also be incorporated into the film, such as melt stabilizers, processing stabilizers, heat stabilizers, light stabilizers, antioxidants, heat aging stabilizers, whitening agents, antiblocking agents, bonding agents, tackifiers, viscosity modifiers, etc. Examples of suitable tackifier resins may include, for instance, hydrogenated hydrocarbon resins. REGALREZ™ hydrocarbon resins are examples of such hydrogenated hydrocarbon resins, and are available from Eastman Chemical (Kingsport, Tenn.). Other tackifiers are available from ExxonMobil (Houston, Tex.) under the ESCOREZ™ designation. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals of under the trade name "Irganox®", such as Irganox® 1076, 1010, or E 201. Moreover, bonding agents may also be added to the film to facilitate bonding of the film to additional materials (e.g., nonwoven web). When employed, such additives (e.g., tackifier, antioxidant, stabilizer, etc.) may each be present in an amount from about 0.001 wt. % to about 25 wt. %, in some embodiments, from about 0.005 wt. % to about 20 wt. %, and in some embodiments, from 0.01 wt. % to about 15 wt. % of the film.

As mentioned herein, water-impermeable substrate 14 may be formed using any one of the conventional processes known to those familiar with elastomeric and/or film formation. The polyolefin polymer and any optional ingredients (e.g., filler) are mixed in and then heated and extruded into a film.

The water-impermeable substrate of the present disclosure may be described as a mono-layer film or, as other types, such as multi-layer films, provided the forming technique is compatible with films described herein. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a blend of a thermoplastic elastomer and semi-crystalline polyolefin. In such embodiments, the skin layer(s) may be formed from any film-forming polymer. If desired, the skin layer(s) may contain a softer, lower melting polymer or polymer blend that renders the layer(s) more suitable as heat seal bonding layers for thermally bonding the film to a nonwoven web. In most embodiments, the skin layer(s) are formed from an olefin polymer such as described above. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

The thickness of the skin layer(s) is generally selected so as not to substantially impair the elastomeric properties of the film. To this end, each skin layer may separately comprise from about 0.5% to about 15% of the total thickness of the film, and in some embodiments from about 1% to about 10% of the total thickness of the film. For instance, each skin layer may have a thickness of from about 0.1 to about 10 micrometers, in some embodiments from about 0.5 to about 5 micrometers, and in some embodiments, from about 1 to about 2.5 micrometers. Likewise, the base layer may have a thickness of from about from about 1 to about 40 micrometers, in some embodiments from about 2 to about 25 micrometers, and in some embodiments, from about 5 to about 20 micrometers.

Typically the water-impermeable substrate 14 will be attached to the outer fibrous substrate 12 and inner fibrous substrate 16 by thermally bonding the three layers together at discrete points (see, e.g., discussion in preceding paragraph as well as U.S. Pat. No. 6,037,281, entitled "Cloth-Like, Liquid-Impervious, Breathable Composite Barrier Fabric," to Mathis, et al.). As noted above, the two fibrous substrates may be bonded or attached to the water-impermeable substrate at discrete locations while the water-impermeable substrate is in a stretched condition, thereby producing undulations when the resulting laminated article is in a relaxed condition. Other known means for bonding and laminating the water-impermeable substrate 14 to fibrous substrates 12, 16 may be used, provided the resulting laminated article 10 has the required properties described herein. For example, the three substrates may be adhesively bonded to one another.

While described herein as using a water-impermeable substrate, it should be understood that, in some embodiments, the substrates and laminated articles can be made from layers that are not water-impermeable without departing from the scope of the present disclosure.

Other additives and ingredients may be added to the water-impermeable substrate 14 provided they do not significantly interfere with the ability of the substrate to function in accordance with the teachings of the present disclosure. Such additives and ingredients can include, for example, antioxidants, stabilizers, and pigments.

While described herein as having three substrate layers, it should be recognized by one skilled in the art that the laminated article can have only two substrates bonded together or can have more than three substrate layers, such as four substrates, five substrates or even six or more substrates without departing from the present disclosure.

Representative Laminated Articles

One or more laminated articles, such as those described above, must be configured into the form of a glove, mitten, sock, sleeve, patch, or other article designed to be fitted to a part of the user's body. Generally the article will be made by cutting at least first and second substrates into appropriate pieces such that the pieces, when attached to one another, form an article having an interior volume into which a portion of a user's body may be inserted.

Figure 2:
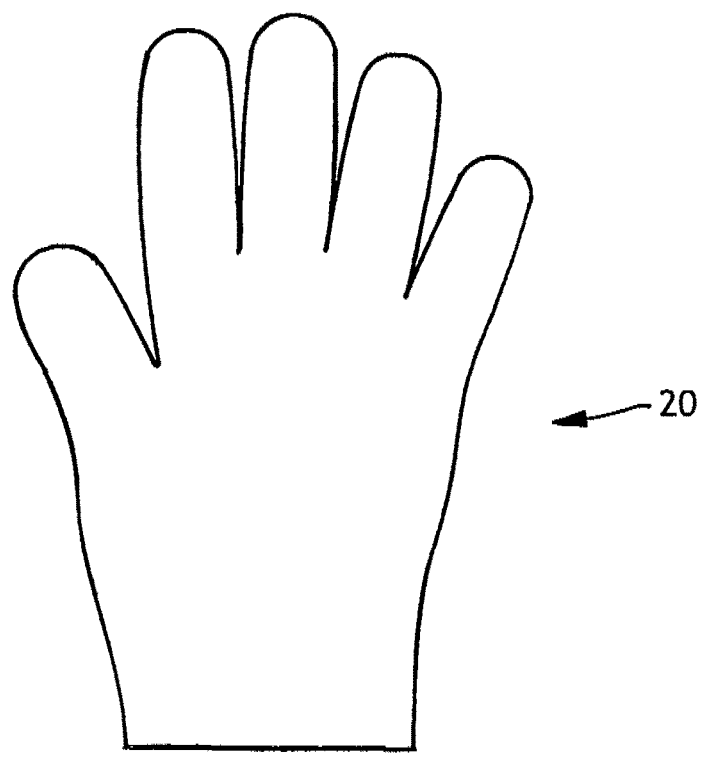
FIG. 2 depicts one embodiment of a substrate for use in a laminated article cut so that the substrate's perimeter defines the shape of a user's hand.
Figure 2A:
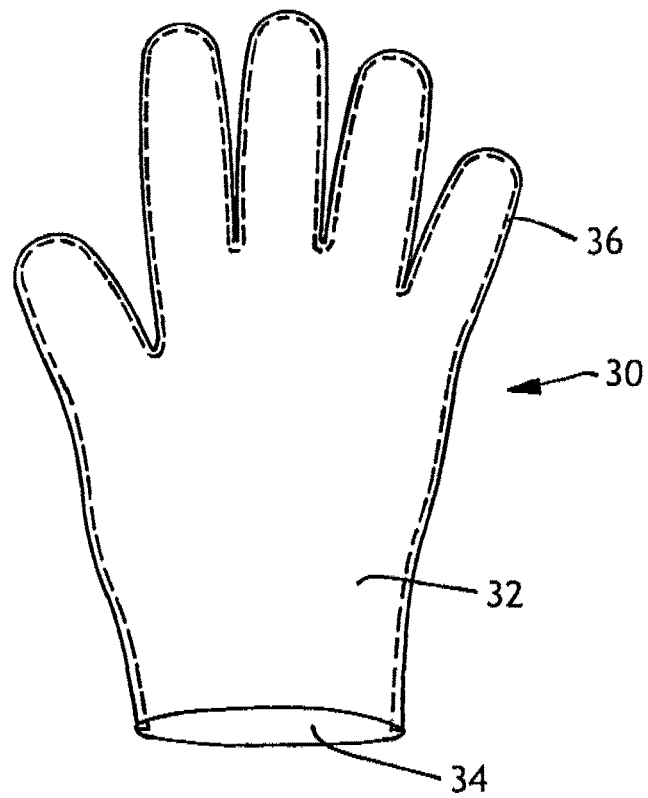
FIG. 2A depicts a laminated article using the substrate of FIG. 2.

FIG. 2 representatively depicts a first substrate 20 cut so that the piece (or substrate) defines a perimeter in the shape of a human hand. FIG. 2A representatively depicts an article 30 comprising a first substrate 32 attached to a second substrate 34 at a location proximate to the perimeters of these two substrates. In this representative illustration, the two substrates are attached to one another mechanically by sewing the pieces together at a location proximate to the perimeters of the two substrates. The resulting article was then inverted so that the seam 36 formed by sewing the substrates together is on the interior of the article. Of course the finished article need not be inverted; the seam can remain on the exterior of the article. Note, too, that the individual substrates need not be joined in a way that produces a seam. The edges of the individual substrates may be butted together, and then, for example, joined and/or welded together using a solvent.

Alternatively, the individual substrates may be butted together, and another material, such as an adhesive or an adhesive tape, used to join the substrates together.

Individual substrates may be cut into a variety of shapes and sizes. Rather than the glove depicted in FIGS. 2 and 2A, the substrates may be cut so that the resulting article is in the shape of a tube, sleeve, mitten, sock, or the like. Any shape is possible, so long as the resulting article defines an interior volume into which a user may insert a portion of his or her body (e.g., a finger, toe, hand, foot, wrist, forearm, etc.) such that a formulation, as described herein below, applied to the interior surface of the article may be transferred to skin or tissue in contact with the interior surface of the article.

The individual substrates need not be sewn together. The individual substrates may also be joined ultrasonically, thermally, adhesively, cohesively, using tape, by fusing the substrates together (e.g., by using an appropriate solvent), by welding the substrates together, or by other approaches. So long as the individual substrates remain attached or connected during normal use of the article, and attachment or connection is such that the formulation on the interior surface of the article is contained within the article (i.e., there is minimal or no leakage of the formulation), any connection or attachment may be used.

Alternatively, a substrate could be prepared in the form of a rectangle, oval or other shape. An adhesive capable of adhering to skin could then be applied to all or part of the perimeter of the shape such that the article could be releasably adhered to skin. The formulation to be transferred to skin could then be coated or deposited on the surface of the article that will contact skin or tissue.

Figure 3:
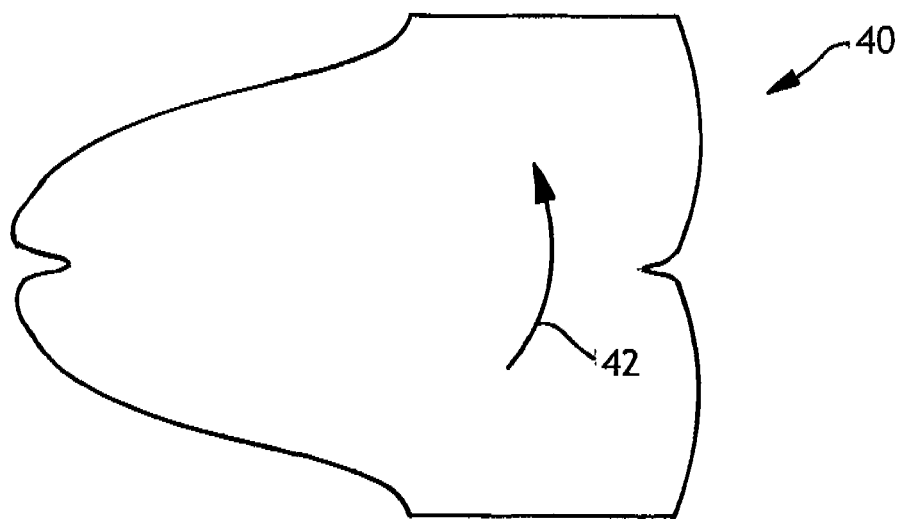
FIG. 3 depicts a second embodiment of a substrate for use in a laminated article cut so as to form a foot-configured laminated article of the present disclosure.
Figure 3A:
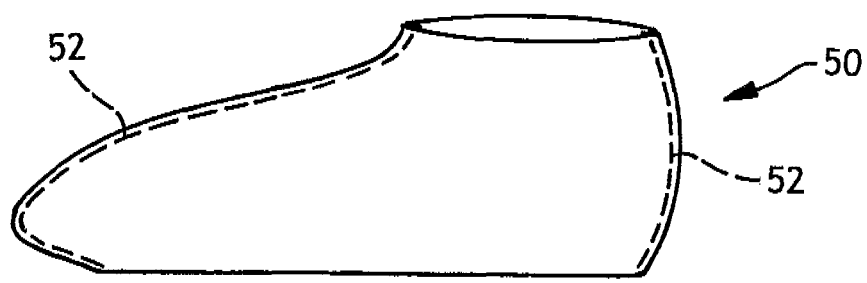
FIG. 3A depicts a laminated article using the substrate of FIG. 3.

Note, too, that an article may be formed from a single piece of a first substrate. FIG. 3 representatively illustrates a first substrate 40 that has been cut in a way that a foot-shaped article may be formed by folding the substrate back on itself (as shown by arrow 42; the bottom half of the shape is folded upward, and on top of, the top half of the shape). FIG. 3A representatively illustrates such a foot-shape article 50 and the resulting seams 52 formed when the substrate 40 (from FIG. 3) is folded back, and attached to, itself. In this representative embodiment, the foot-shape article was inverted after the substrate was attached to itself so that the seams were on the inside of the article. As with two (or more) substrates that may be joined together to form an article of the present disclosure, a single substrate may be joined to itself using any of the approaches discussed above.

Representative Formulations for Use with the Substrates and Laminated Articles made therefrom As noted above, the formulations for use with the substrates and laminated articles of the present disclosure are capable of improving the user's skin health and hygiene without interfering with the mechanical properties such as the elastomeric properties and overall integrity of the substrate and/or article.

Generally, the formulations of the present disclosure include at least one cosmetic carrier. As used herein, the term "cosmetic carrier" refers to both hydrophilic and hydrophobic carriers that do not interfere with the mechanical properties of the substrates and/or laminated articles made therefrom. Suitable hydrophilic carriers include, but are not limited to, propylene glycol, butylene glycol, dipropylene glycol, glycerin, glycereth-18 ethylhexanoate, glycereth-18, betaine, diglycerin, glycol, inositol, meadowfoamamidopropyl betaine, ethyl alcohol, isopropyl alcohol, polyethylene glycol with varied molecular weights, sorbitol, xylitol, urea, tripropylene glycol, sodium PCA, glycereth-7 glycolate, diglycereth-7 malate, 2,3-butanediol, propanediol, xylose, almond oil PEG-6 esters, apricot kernel oil PEG-6 esters, argan oil PEG-8 esters, argan oil polyglyceryl-6 esters, dimethicone, silicones with suitable levels of polypropylene glycol functionality such as PPG-12 dimethicone, silicones with suitable levels polyethylene glycol functionality such as PEG-12 dimethicone, PEG-10 dimethicone and silicones which combine both functionalities in varying ratios such as PEG/PPG-5/3 trisiloxane, PEG/PPG-8/26 dimethicone, PEG/PPG-20/15 dimethicone, bis-PEG-4 dimethicone, bis-PEG-12 dimethicone, bis-PEG/PPG-14/14 dimethicone, bis-PEG/PPG-18/6 dimethicone, bis-PEG/PPG-20/20. Suitable hydrophobic substances include, but are not limited to, PEG-3 dimethicone, PEG-8 dimethicone, cyclomethicone, dimethcione, cetyl dimethicone, caprylyl methicone, ethyl trisiloxane, trimethylsiloxyamodimethicone, stearyl dimethicone, butylene glycol behenate, butylene glycol diisononanoate, butylene glycol laurate, butylene glycol myristate, butylene glycol oleate, butylene glycol palmitate, butylene glycol stearate, butyl isostearate, butyl myristate, butyloctyl behenate, butyloctyl benzoate, butyloctyl cetearate, butyloctyl palmitate, butyl oleate, butyl stearate $C_{14-15}$ alcohols, $C_{18-28}$ alkyl acetate, $C_{12-15}$ alkyl benzoate, $C_{16-17}$ benzoate, $C_{30-45}$ alkyl cetearyl dimethicone crosspolymer, $C_{32}$ alkyl dimethicone, $C_{30-45}$ alkyl dimethicone/polycyclohexene oxide crosspolymer, $C_{12-13}$ alkyl ethylhexanoate, $C_{12-15}$ alkyl ethylhexanoate, $C_{14-18}$ alkyl ethylhexanoate, $C_{12-13}$ alkyl lactate, $C_{12-15}$ alkyl lactate, $C_{20-24}$ alkyl methicone, $C_{24-28}$ alkyl methicone, calodendrum capense nut oil, calophyllum tacamahaca seed oil, cetearyl dimethicone/vinyl dimethicone crosspolymer, cetearyl ethylhexanoate, cetearyl isononanoate, cetearyl nonanoate, cetearyl palmitate, cetrimonium laureth-12 succinate, cetyl acetate, cetyl caprylate, cetyl $C_{12-15}$ pareth-8 carboxylate, cetyl dimethicone, cetyl dimethicone/bis-vinyldimethicone crosspolymer, cetyl dimethyloctanoate, cetyl esters, cetyl ethylhexanoate, cetyl glyceryl ether, cetyl glycol, cetyl glycol isostearate, cetyl isononanoate, cetyl lactate, cetyl laurate, cetyl oleate, cetyloxy dimethicone, $C_{12-15}$ pareth-3 benzoate, $C_{12-15}$ pareth-9 hydrogenated tallowate, $C_{11-15}$ pareth-3 oleate, $C_{12-15}$ pareth-12 oleate, $C_{11-15}$ pareth-3 stearate, $C_{11-15}$ pareth-12 stearate, dibutyl adipate, dibutyldecyl IPDI, dibutyloctyl IPDI, dibutyloctyl malate, dibutyloctyl sebacate, dibutyl sebacate, Ddi-$C_{12-15}$ alkyl adipate, di-$C_{12-15}$ alkyl fumarate, di-$C_{12-13}$ alkyl malate, di-$C_{12-15}$ alkyl maleate, di-$C_{12-13}$ alkyl tartrate, —$C_{14-15}$ alkyl tartrate, dicaprylyl carbonate, dicaprylyl ether, dicaprylyl maleate, dicetyl adipate, dicocoyl pentaerythrityl distearyl citrate, diethyl adipate, isobutyl myristate, isobutyl palmitate, isobutyl pelargonate, isobutyl stearate, isobutyl tallowate, isocetyl alcohol, isocetyl ethylhexanoate, isocetyl isodecanoate, isocetyl isostearate, isocetyl laurate, isocetyl linoleoyl stearate, isocetyl palmitate, isocetyl stearate, lanolin, lanolin oil, lanolin wax, lauryl lactate, neopentyl glycol diheptanoate, neopentyl glycol diisononanoate, neopentyl glycol dilaurate, octyldodecyl ethylhexanoate, octyldodecyl lactate, octyldodecyl neodecanoate, octyldodecyl neopentanoate, PPG-3 benzyl ether myristate, PPG-1-ceteth-1, PPG-1-ceteth-5, PPG-1-ceteth-10, PPG-1-ceteth-20, sunflower oil, safflower oil, mineral oil and jojoba oil diisoamyl malate, diethylhexyl malate, dibutyloctyl malate, dimethyl capramide, diethylhexyl 2,6 napthalate, N,N-dimethyldesamide, diisopropyl adipate, phenethyl benzoate, octocrylene, PEG-7 methyl ester, and combinations thereof. Particularly preferred cosmetic carriers include silicone-containing compounds, esters, amides, and ethers. Other suitable cosmetic carriers could be utilized and are listed in the CTFA Ingredient Dictionary (2007). The selection of suitable cosmetic carriers will vary depending on the substrate that is chosen and must be chosen so as to ensure that the properties of the substrate are maintained for strength and integrity. Similarly, the nonwoven substrates may be selected based on their inherent resistance to loss of integrity based on the cosmetic carriers and the formulation chosen.

Suitable silicon-containing compounds include silicone derivatives such as, for example, cyclomethicone; dimethicone; cetyl dimethicone; PEG-3 dimethicone; PEG/PPG-20/23 dimethicone; PEG/PPG-8/26 dimethicone; PEG/PPG-20/15 dimethicone; PEG-8 dimethicone; PPG-12 dimethicone; PEG-10 dimethicone; caprylyl methicone; ethyl trisiloxane; PEG-8 trisiloxane; PEG/PPG-5/3 trisiloxane; trimethylsiloxyamodimethicone; stearyl dimethicone; and combinations thereof.

Suitable esters, amides, and ethers include, for example, diethylhexyl 2,6 napthalate, PPG-3 benzyl ether myristate, dimethyl capramide, dibutyl adipate, diisopropyl adipate, lauryl lactate, diethylhexyl malate, phenethyl benzoate, octocrylene, PEG-7 methyl ester, and combinations thereof.

Typically, when the cosmetic carrier includes a silicone derivative, ester, amide, or ether, the cosmetic carrier includes from about 0.1% to about 95% by weight silicone derivative, ester, amide, or ether. More suitably, the cosmetic carrier includes from about 5% to about 50% by weight silicone derivative, ester, amide, or ether, and even more suitably, from about 15% to about 35% by weight silicone derivative, ester, amide, or ether.

The balance of the cosmetic carrier can be made of water, other suitable oils, emulsifiers, emollients, humectants, occlusive agents, sunscreens, antioxidants, film formers, rheology modifiers, preservatives, chelants, abrasives, and combinations thereof.

The amount of cosmetic carrier in the formulation will typically depend on the other components and amounts of components in the formulation. Furthermore, the type of desired functional and mechanical properties of the formulation as more fully described below will also determine the amount of cosmetic carrier desired in the formulation.

Typically, the cosmetic carrier will be present in the formulation in an amount of from about 0.1% (by weight formulation) to about 95% (by weight formulation). More suitably, the cosmetic carrier is present in an amount of from about 5% (by weight formulation) to about 50% (by weight formulation), and even more suitably, from about 15% (by weight formulation) to about 35% (by weight formulation).

The formulation may further include other components to provide one or more functional, aesthetic, or mechanical benefits to the formulation and, ultimately, to the user of the formulation and substrate having the formulation thereon. Exemplary optional components may include for example: emollients; skin barrier enhancers; humectants; rheology enhancers; and combinations thereof. Emollients lubricate, sooth, and soften the skin surface. Exemplary emollients include oily or waxy ingredients such as esters, ethers, fatty alcohols, hydrocarbons, silicones, and the like, and combinations thereof.

Skin barrier enhancers, also referred to as occlusive materials, increase the water content of the skin by blocking water evaporation. These materials generally include lipids which tend to remain on the skin surface or hydrocarbons such as petrolatum and wax.

Humectants are hydroscopic agents that are widely used as moisturizers. Their function is to prevent the loss of moisture from the skin and to attract moisture from the environment. Common humectants include, for example, glycerin, butylene glycol, betaine, sodium hyaluronate, and the like, and combinations thereof.

Rheology enhancers may help increase the melt point viscosity of the formulation so that the formulation readily remains on the surface of the substrate and/or laminated article and does not substantially migrate into the interior of the substrate, while substantially not affecting the transfer of the formulation to the skin. The rheology enhancers help the formulation to maintain a high viscosity at elevated temperatures, such as those encountered during storage and transportation. Additionally, rheology enhancers can influence the overall consistency and skin feel of the formulation.

Suitable rheology enhancers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/proplylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers. Other suitable examples of oil-soluble rheology enhancers include, but are not limited to, aluminum stearate, aluminum tristearate, arachidyl alcohol, arachidyl behenate, behenyl alcohol, $C_{8-22}$ alkyl acrylate/butyl dimethicone methacrylate copolymer, $C_{12-22}$ alkyl acrylate/hydroxyethylacrylate copolymer, $C_{18-38}$ alkyl, $C_{24-54}$ acid ester, $C_{20-24}$ alkyl dimethicone, $C_{24-28}$ alkyl dimethicone, $C_{30-60}$ alkyl dimethicone ceresin, cerotic acid, cetearyl alcohol, cetearyl dimethicone/vinyl dimethicone crosspolymer, cetyl alcohol, cetyl glycol, dibehenyl fumarate, hydrogenated polyisobutene, hydrogenated oils, isocetyl alcohol, isocetyl stearoyl stearate, isophthalic acid/pentaerythritol crosspolymer benzoate/isostearate, isostearyl alcohol, isostearyl stearoyl stearate, jojoba alcohol, lanolin alcohol, lanolin wax, neopentyl glycol dicaprate, neopentyl glycol dicaprylate/dicaprate, neopentyl glycol dicaprylate/dipelargonate/dicaprate, neopentyl glycol diethylhexanoate, neopentyl glycol diheptanoate, neopentyl glycol diisostearate, neopentyl glycol dilaurate, ozokerite, palm alcohol, palm kernel alcohol, paraffin, pentaerythrityl tetramyristate, pentaerythrityl tetraoleate, pentaerythrityl tetrapelargonate, pentaerythrityl tetrastearate, pentaerythrityl trioleate, silica, synthetic beeswax, synthetic candelilla wax, synthetic carnauba, vinyldimethyl/trimethylsiloxysilicate, stearyl dimethicone crosspolymer VP/eicosene copolymer and VP/hexadecene copolymer. Water soluble or water dispersable rheology modifiers include, but are not limited to, acetamide MEA, acrylamide/ethalkonium chloride acrylate Copolymer, acrylamide/ethyltrimonium chloride acrylate/ethalkonium chloride acrylate copolymer, acrylamides copolymer, acrylamide/sodium acrylate copolymer, acrylates/acetoacetoxyethyl methacrylate copolymer, acrylates/beheneth-25 methacrylate copolymer, acrylates/$C_{10-30}$ alkyl acrylate crosspolymer, acrylates/ceteth-20 itaconate copolymer, acrylates/ceteth-20 methacrylate copolymer, acrylates/laureth-25 methacrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/vinyl neodecanoate crosspolymer, acrylic acid/acrylonitrogens copolymer, agar, agarose, algin, alginic acid, ammonium acryloyldimethyltaurate/vinyl formamide copolymer, ammonium acryloyldimethyltaurate/VP copolymer, ammonium alginate, ammonium chloride, amylopectin, *Avena sativa* (oat) kernel flour, bentonite, calcium alginate, calcium carrageenan, $C_{20-40}$ alkyl stearate, carbomer, carboxybutyl chitosan, carboxymethyl hydroxyethylcellulose, carboxymethyl hydroxypropyl guar, cassia Gum, cellulose gum, cetyl hydroxyethylcellulose, $C_{12-14}$ hydroxyalkyl, hydroxyethyl sarcosine, cocamide DEA, cocamide MEA, decyl HDI/PEG-180 crosspolymer, decyltetradeceth-200 isostearate, dextrin, dimethicone/PEG-10 crosspolymer, dimethicone/PEG-15 crosspolymer, dimethylacrylamide/ethyltrimonium chloride methacrylate copolymer, disteareth-75 IPDI, disteareth-100 IPDI, gelatin, gellan gum, hectorite, hydrated silica, hydrolyzed cellulose gum, hydroxybutyl methylcellulose, hydroxyethylcellulose, hydroxyethyl ethylcellulose, hydroxypropyl chitosan, hydroxypropyl guar, hydroxypropyl methylcellulose, hydroxypropyl methylcellulose stearoxy ether, hydroxypropyl starch, hydroxypropyl starch phosphate, hydroxypropyl xanthan gum, isopolyglyceryl-3 dimethicone, isopolyglyceryl-3 dimethiconol, lauryl hydroxysultaine, lauryl/myristyl glycol hydroxypropyl ether, lauryl PEG-9 polydimethylsiloxyethyl dimethicone, lauryl polyglyceryl-3 polydimethylsiloxyethyl dimethicone, levan, magnesium alginate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, montmorillonite, myristamidopropyl hydroxysultaine, oatamidopropyl betaine, octacosanyl glycol isostearate, octadecene/MA copolymer, pectin, PEG-150/decyl alcohol/SMDI copolymer, PEG-175 diisostearate, PEG-190 distearate, PEG-15 glyceryl tristearate, PEG-140 glyceryl tristearate, PEG-240/HDI copolymer bis-decyltetradeceth-20 ether, PEG-100/IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14MPEG-20M, PEG-23M, PEG-25M, PEG-45M, PEG-65M, PEG-90M, PEG-115M, PEG-160M, PEG-180M, PEG-120 methyl glucose triisostearate, PEG-120 methyl glucose trioleate, PEG-150 pentaerythrityl tetrastearate, PEG/PPG-120/10 trimethylolpropane trioleate, PEG/PPG-120/10 trimethylpropane trioleatePEG-150/stearyl alcohol/SMDI copolymer, polyacrylate-3, polyacrylate-10, polyacrylate-11, polyacrylic acid, polycyclopentadiene, polyester-5, polyether-1, polyethylene/isopropyl maleate/MA copolyol, polyglycerin-20, polyglycerin-40, polyglyceryl-3 disiloxane dimethicone polyglyceryl-3 polydimethylsiloxyethyl dimethicone, polyquaternium-86, polyvinyl alcohol, potassium polyacrylate, potato starch modified, PVP montmorillonite, sodium acrylates/acrylonitrogens copolymer, sodium acrylates copolymer, sodium acrylates crosspolymer, sodium acrylate/sodium acrylamidomethylpropane sulfonate copolymer, sodium acrylate/sodium acryloyldimethyl taurate/acrylamide copolymer, sodium acrylates/vinyl isodecanoate crosspolymer, sodium acrylate/vinyl alcohol copolymer, sodium acryloyldimethyl taurate/acrylamide/VP copolymer, sodium carboxymethyl beta-glucan, sodium carboxymethyl starch, sodium carrageenan, sodium cellulose sulfate, sodium chloride, sodium hydroxypropyl starch phosphate, sodium isooctylene/MA copolymer, sodium polyacrylate, sodium silicoaluminate, sodium starch octenylsuccinate, sodium sulfate, steareth-100/PEG-136/HDI copolymer, tapioca starch, TEA-alginate, TEA-carbomer, trehalose hydroxypropyltrimonium chloride, tridecyl alcohol, undecyl alcohol, wheat germamidopropyl betaine, xanthan gum, yeast, polysaccharides, and *Zea Mays* (corn) starch.

Still other optional components that may be desirable for use with the formulation of the present disclosure include those cosmetic and pharmaceutical ingredients commonly used in the skin care industry. Examples include abrasives, absorbents, aesthetic components (fragrances, pigments, colorings/colorants), essential oils, skin sensates, astringents (e.g., clove oil, menthol, camphor, eucalyptus oil, eugenol, menthyl lactate, witch hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents, skin soothing and/or healing agents (e.g., panthenol and derivatives thereof), aloe vera, pantothenic acid and derivatives thereof, allantoin, bisabolol, dipotassium glycyrrhizinate, skin treating agents, sunscreens, thickeners, and vitamins, and combinations thereof. Examples of these and other agents are disclosed in The CTFA Cosmetic Ingredient Handbook, 12$^{th}$ Ed. (2007), which is hereby incorporated by reference to the extent that it is consistent herewith.

The amounts of the optional components will depend on the cosmetic carriers used and the amounts of the cosmetic carriers in the formulations as well as the desired benefits of the formulations.

As noted above, the formulations used in the substrates and articles of the present disclosure typically include greater than 5% (by weight formulation) water, and preferably, are emulsion formulations. More suitably, the formulations include greater than about 10% (by weight formulation) water, even more suitably, greater than about 50% (by weight formulation) water; and even more suitably, greater than about 60% (by weight formulation) water.

Suitable emulsion formulations include, for example, water-in-silicone formulations, water-in-oil emulsions, and oil-in-water emulsions. Also suitable are emulsions within emulsions, such as water-in-oil-in-water emulsions and the like. Particularly preferred are water-in-silicone emulsions.

The amount of water in the emulsions will vary depending on the type of emulsion, specifically, on the type of emulsifier used and the type of oil chosen. Suitably, when the formulation is an emulsion, the emulsion is made of from about 50% to about 85% w/w water. More suitably, the emulsion is made of from about 65% to about 75% w/w water.

Typically, the formulation is applied to the surface of the substrate and will be present in an amount of at least about 10% w/w of the substrate. More suitably, the formulation will be applied to the substrate from about 50% w/w to about 300% w/w; even more suitably, from about 50% w/w to about 200% w/w; and even more suitably, from about 50% w/w to about 100% w/w.

Physical Functional and Mechanical Properties of the Formulations and Substrates having the Formulations Applied Thereon As noted above, no matter the carrier used or the optional components that may be included in the formulation, the overall formulation for use with the substrates and/or articles of the present disclosure should have a dielectric constant of less than 40.0. It has generally been known that high concentrations of oil components in formulations having low polarity, or lower dielectric constants, are known to substantially reduce the strength and overall integrity of the substrates or webs to which the formulations are applied. Particularly, dielectric constants are a good indicator of polarity of a composition as the dielectric constant is a measure of both inherent and inducible dipole moments. As the dielectric constants of the components are increased, however, the load levels, and thus, the compatibility between the components in the formulation and the substrates are also increased. Accordingly, it has conventionally been believed that when using emulsion formulations, and other oil-containing formulations, the levels of oil should be kept low so as to keep the dielectric constant high, allowing the formulations to remain compatible with the substrates.

Surprisingly, however, it has been disclosed that the compatibility of formulations using the cosmetic carriers discussed above behave independently of the formulation's overall dielectric constants. Thus, formulations having lower dielectric constants have the unexpected result of still being compatible with the substrates and not causing delamination or deterioration of the properties of the substrate. Accordingly, the formulations used in the substrates and articles of the present disclosure typically have lower dielectric constants. For example, as noted above, the formulations have a dielectric constant of from less than about 40.0, and more suitably, from about 10.0 to about 35.0.

Measurement of a dielectric constant of a liquid or composition can be performed by various sensors, such as immersion probes, flow-through probes, and cup-type probes, attached to various meters, such as those available from the Brookhaven Instruments Corporation of Holtsville, N.Y. (e.g., model BI-870) and the Scientifica Company of Princeton, N.J. (e.g. models 850 and 870). For consistency of comparison, preferably all measurements for a particular filter system are performed at substantially the same sample temperature, e.g., by use of a water bath.

For example, in one embodiment, the dielectric constant values were obtained at a 23° C. (73.4° F.) using the Brookhaven BI-870 meter. The BI-870 meter has two selectable sensitivity ranges: 1-20 and 1-200, and has an absolute accuracy of about ±2% and linearity of better than 0.2%. The measure signal applied to the outer cylinder of the probe is a low-distortion sine wave at a frequency of about 10 kHz. The amplitude is approximately 7 volts rms on the 1-20 range and 0.7 volts on the 1-200 range. The frequency is crystal-controlled and is, therefore, stable to approximately 1 part in 105. The dielectric constant of the liquid sample is determined by measuring the current between the outer and inner cylinders of the probe. With a stable voltage source and precisely known probe parameters, it is possible to display the dielectric constant directly. Calibration is simple using the back panel adjustment with a liquid of known dielectric constant.

It is important to note that obtaining accurate, repeatable measurements of dielectric constant of emulsion formulations is dependent both on the stability of the emulsion formulation (Reddy and Dorle, Cosmetic & Toiletries, October, 1984, vol. 99 (10), page 67)), as well as the presence of conductive compounds or impurities (U.S. Pat. No. 3,675,121 issued to Don Thompson on Jul. 4, 1972). Such compounds, particularly salts, may very well be an intended component of the formulation. Removing these conductive compounds may therefore be necessary to obtain accurate, repeatable measurements.

Using formulations having increased compatibility with the substrates and/or articles, allows for substrates having improved mechanical properties and overall improved integrity. Particularly, the substrates incorporating the formulations described herein, typically retain at least about 40% of the tension of the untreated substrate at a typical target elongation of 30% of the original length of the substrate. As used herein "of the tension of untreated substrate at 30% target elongation" refers to the percent load retained by the substrate treated with formulation as compared to the untreated substrate at 30% elongation. For elastomeric substrates in general, any given elongation beyond 5% that is representative of a typical elongation during use of the substrate may be used for comparison of treated and untreated substrates, up to the "stretch-to-stop" of the untreated substrate. As used herein, "stretch-to-stop" refers to the point at which the non-elastomeric components of a substrate inherently prevent further or excessive stretching of the elastomeric substrate, as described more fully in U.S. Pat. No. 4,720,415, issued to Vander Wielen, et al. (Jan. 19, 1988), which is incorporated herein by reference to the extent that it is consistent herewith. More particularly, the non-elastomeric components act as a "stop" to prevent further or excessive stretching of the substrate under the effect of stretching forces which are less than the failure strength of the non-elastomeric components.

More suitably, the substrates incorporating the formulations described herein, typically retain at least about 75% of the tension of the untreated substrate at 30% elongation, and even more suitably, the substrates incorporating the formulations described herein, typically retain at least about 90% of the tension of the untreated substrate at 30% elongation.

The following test procedures can be used to determine the effect of the formulations on the mechanical properties of the substrates.

Multi-Cycle Stress/Strain Test for Raw Materials

The Multi-cycle Stress/Strain Test is a two-cycle elongation and recovery test used to measure the elongation and recovery characteristics of elastic raw materials and elastic material composites. In particular, the test may be used to determine what effects, if any, the application of the described formulations to the substrates have on the elongation and recovery characteristics thereof. Deterioration of substrate properties measured by this test are those that manifest as a loss of tension, or resistance to elongation, which may result in extreme elongation on application of a force, as with sagging.

The test measures load values of a test sample placed under a particular amount of strain (e.g., elongated to a particular elongation). Such load values are determined during both the elongation and recovery phases of the test, and during each of the two cycles. For this application, the load values at 30% elongation on the first cycle are of particular interest. The average of the values obtained for the load at 30% elongation with the formulation added to the substrate are compared to the average of the values obtained for the load at 30% elongation with the untreated substrates to determine the load retained at 30% elongation. In general, a decrease in the amount of the load retained after treatment indicates a negative impact on the elastic characteristics of the substrate, even in the absence of visible deterioration or delamination of the substrate.

Sample Preparation

Six samples of the test specimen should be subjected to the Multi-cycle Stress/Strain Test, three samples of the untreated substrate and three samples of the substrate treated with the formulation, and the results for each set of three samples should be averaged. Care should be taken to avoid stretching the substrates during the process of sample preparation. A sample formulation is applied to a substrate and/or laminated article using the substrate to be tested in an amount of about 100% w/w. The substrate and/or article is aged at 55° C. for one week. Following aging, the substrates and/or articles are equilibrated overnight according to the Technical Association of the Pulp and Paper Industry at 50% relative humidity and 73° F. (22.8° C.) (TAPPI) and cut into one inch (25 mm) by five inch (127 mm) strips. Where the specimen is taken from a manufactured article having a width greater than 1 inch (25 mm), the samples should be cut from the midline of the specimen, e.g., samples which include the widthwise edges of the article should be avoided to reduce the risk that edge effects may cause inconsistent results in testing.

Test Apparatus and Materials

The following test apparatus and materials are used to conduct the Multi-cycle Stress/Strain Test.

1) Constant Rate of Extension (CRE) tensile tester: MTS tensile tester model SYNERGIE 200, available from MTS Systems Corporation, Eden Prairie, Minn., U.S.A.

2) Load cells: a suitable cell selected so that the majority of the peak load values fall between the manufacturer's recommended ranges of the load cell's full scale value. Load cell model 100N available from MTS Systems Corporation is preferred.

3) Operating software and data acquisition system: MTS TESTWORKS for WINDOWS software version 4, available from MTS Systems Corporation.

4) Grips: pneumatic-action grips, top and bottom, identified as part number 2712-003 available from Instron Corporation, Canton, Mass., U.S.A.

5) Grip faces: 1 inch (25.4 mm) by 3 inch (76.2 mm) faces, rubberized top and bottom, Instron part number S1-12465, available from Instron Corporation, or equivalent.

Test Conditions

The instruments used should be calibrated as described in the manufacturer's instructions for each instrument.

The tensile tester conditions are as follows:
Gauge separation—4 inches (102 mm)
Crosshead speed—20 inches/minute (508 mm/minute)
Cycle elongation—100%
Number of cycles—2

Test Method

Using the tensile frame controls for crosshead position, move the grips to provide a gauge separation (distance between grips) of 4 inches (102 mm). Set the crosshead position to zero at this separation for accurate calculation of the elongation measurement points. Place the sample to be tested lengthwise so that it is centered between the grips, held in a centered position within each grip, and oriented correctly (e.g., with the long edges of the sample perpendicular to the grip faces). Close the grips on the sample, holding the sample in such a way as to minimize slack in the sample without placing the sample under tension.

Ensure that the load at this point is less than 10 grams-force. If the load is greater than 10 grams-force, release the lower grip and zero the load cell. Re-close the lower grip, again ensuring that the sample is neither under tension nor buckled with excessive slack. Continue checking the starting load and following the above procedure until the starting load is within the desired range.

Run the two cycle test using the above parameters. When the test is complete, save the data to a sample file. Remove the sample from the grips. Run the above procedures for the remaining samples of a given specimen. The data for all samples should be saved to a single file.

Report the data for each sample as follows: load values in grams-force at 30% and 60% elongation, and the averages and standard deviations of each.

The above test procedures are conducted for all of the samples of the treated substrate and all of the samples of the untreated substrate. The retention of load at a given elongation X % is calculated by the following formula:

[(average of load values for treated substrate at elongation X %)×100]/[(average of load values for untreated substrate at elongation X %)]

180-Degree Peel (T-Peel) Strength Test for Laminates

The 180-Degree Peel Strength Test is used to measure the attachment strength between layers of a laminated substrate when separated at an approximate 180-degree angle. In particular, the test may be used to determine what effects, if any, the application of the described formulations to the substrates have on the lamination strengths thereof. The test measures the force required to pull the plies apart. For this application, peak load values are of particular interest for comparing the effects of different formulations. The average of the peak load values obtained with the formulation added to the substrate are compared to the average of the peak load values obtained with the untreated substrate to determine the peak load retained. In general, a decrease in the amount of the peak load retained after treatment indicates a negative impact on the lamination strength of the material, even in the absence of visible delamination of the substrate.

Sample Preparation

Six samples of the test specimen should be subjected to the T-Peel Test, three samples of the untreated substrate and three samples of the substrate treated with the formulation, and the results for each set of three samples should be averaged. Care should be taken to avoid stretching the substrates during the process of sample preparation. A sample formulation is applied to a substrate and/or laminated article using the substrate to be tested in an amount of about 100% w/w. The substrate and/or article is aged at 55° C. for one week. Following aging, the substrates and/or articles are equilibrated overnight according to the Technical Association of the Pulp and Paper Industry at 50% relative humidity and 73° F. (22.8° C.) (TAPPI) and cut into one inch (25 mm) by seven inch (178 mm) strips. Where the specimen is taken from a manufactured article having a width greater than 1 inch (25 mm), the samples should be cut from the midline of the specimen, e.g., samples which include the widthwise edges of the article should be avoided to reduce the risk that edge effects may cause inconsistent results in testing. Each specimen should be cut individually.

Test Apparatus and Materials

The following test apparatus and materials are used to conduct the T-Peel Test.

1) Constant Rate of Extension (CRE) tensile tester: MTS tensile tester model SYNERGIE 200, available from MTS Systems Corporation, Eden Prairie, Minn., U.S.A.

2) Load cells: a suitable cell selected so that the majority of the peak load values fall between the manufacturer's recommended ranges of the load cell's full scale value. Load cell model 100N available from MTS Systems Corporation is preferred.

3) Operating software and data acquisition system: MTS TESTWORKS for WINDOWS software version 4, available from MTS Systems Corporation.

4) Grips: pneumatic-action grips, top and bottom, identified as part number 2712-003 available from Instron Corporation, Canton, Mass., U.S.A.

5) Grip faces: 1 inch (25.4 mm) by 3 inch (76.2 mm) faces, rubberized top and bottom, Instron part number S1-12465, available from Instron Corporation, or equivalent.

6) Line contact grip faces (2 needed): 76.2 mm by 2.3 mm faces, Kimberly Clark item number 1600068, available from Kimberly-Clark Worldwide, Inc. (Neenah, Wis.); used to prevent slippage of the material.

Test Conditions

The instruments used should be calibrated as described in the manufacturer's instructions for each instrument.

The tensile tester conditions are as follows:
Gauge separation—1.5 inches (38 mm)
Crosshead speed—20 inches/minute (508 mm/minute)
Test End Point—6.5 inches (165 mm)

Test Method

Using the tensile frame controls for crosshead position, move the grips to provide a gauge separation (distance between grips) of 1.5 inches (38 mm). Set the crosshead position to zero at this separation. Manually separate the plies of the laminate for approximately 25 mm along the length of the sample from one end. Place the sample to be tested lengthwise so that one ply is centered between the upper grips, and the other ply is centered between the lower grips. Close the upper grips on the sample, and then close the lower grips on the sample. Position the sample in such a way as to minimize slack in the sample without placing the sample under tension.

Ensure that the load at this point is less than 10 grams-force. If the load is greater than 10 grams-force, release the lower grip and zero the load cell. Re-close the lower grip, again ensuring that the sample is neither under tension nor buckled with excessive slack. Continue checking the starting load and following the above procedure until the starting load is within the desired range.

Run the peel test using the above parameters. When the test is complete, save the data to a sample file. Remove the sample from the grips. Run the above procedures for the remaining samples of a given specimen. The data for all samples should be saved to a single file.

Report the data for each sample as follows: peak load values in grams-force, and the averages and standard deviations of each.

The above test procedures are conducted for all of the samples of the treated substrate and all of the samples of the untreated substrate. The retention of load is calculated by the following formula:

[(average of load values for treated substrate)×100]/
[(average of load values for untreated substrate)]

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this Example, various formulations were applied to a spunbond-film-spunbond laminated article. The degree of compatibility of the formulations and article were then determined.

The laminated article sample (140 gsm) was made by sandwiching an elastomeric film substrate between two 50% necked spunbond nonwoven substrates of 0.75 osy each. The elastomeric film layer was comprised of 96% by weight Vistamaxx™ 1100 resin (commercially available from ExxonMobil, Houston, Tex.) and 4% by weight SCC 11692, which is a filler compound available from Standridge Color Corp. (Social Circle, Ga.), which contains calcium carbonate blended with polypropylene and polypropylene random copolymers. The substrates were thermally point bonded together with the film layer in an extended state, and the resulting composite sample was allowed to retract to give a 3-D texture.

The outer nonwoven layers were formed from a thermoplastic composition that contains at least one copolymer of propylene and α-olefin. Such propylene copolymers are commercially available under the designations VISTAMAXX™ from ExxonMobil Chemical Company (Houston, Tex.); FINA™ 8573 from Atofina Chemicals (Feluy, Belgium); TAFMER™ from Mitsui Petrochemical Industries; and VERSIFY™ available from Dow Chemical Company (Midland, Mich.).

Any of a variety of known techniques may generally be employed to form the propylene copolymers. For instance, the copolymers was formed using a single-site coordination catalyst (i.e., metallocene catalyst), as described in U.S. Pat. No. 7,105,609 issued to Datta, et al. (Sep. 12, 2006); U.S. Pat. No. 6,500,563 issued to Datta, et al. (Dec. 31, 2002); U.S. Pat. No. 5,539,056 issued to Yang, et al. (Jul. 23, 1996); and U.S. Pat. No. 5,596,052 issued to Resconi, et al. (Jan. 21, 1997).

Various formulations were then applied to the article samples. The experimental formulations for application are shown in Table 1A & 1B.

TABLE 1A

Water/Silicone Emulsion (K158-010)

| Supplier | Tradename | INCI name | Weight (%) | Weight (g) |
|---|---|---|---|---|
| Phase A | | | | |
| NA | NA | Water | 35.1 | 157.95 |
| COGNIS Co. (Cincinnati, Ohio) | Elestab FL-15 | Butylene Glycol, Glycerin Methylparaben, Chlorophenesin | 2.0 | 9.0 |
| Mallinckrodt (St. Louis, Missouri) | NA | Magnesium Sulfate Heptahydrate | 0.8 | 3.6 |
| Rita (Washington DC) | NA | Propylene Glycol | 5.0 | 22.5 |
| Dow Chemical (Joliet, Illinois) | Versene NA2 | Disodium EDTA | 0.1 | 0.45 |
| Phase B | | | | |
| Dow Corning (Midland, Michigan) | DC 200 10 cst | Dimethicone | 50 | 225 |
| Barnet (Herfordshire, UK) | NET-WO | Cyclopentasiloxane, PEG-10 Dimethicone, Distearyldimonium Hectorite | 7.0 | 31.5 |
| Total | | | 100 | 450 |

To prepare the water/silicone emulsion, the water was warmed to a temperature of about 122° F. (50° C.). The remaining ingredients of Phase A were then mixed until uniform. NET-WO was then dispersed into the DC 200 10 cst at a temperature of 122° F. (50° C.), and Phase A was added to Phase B under gradual homogenization (approximately 10 to 15 grams at a time). The phases were mixed until the free liquid was fully incorporated into the formulation. The formulation was allowed to cool to room temperature and then homogenized again.

TABLE 1B

Global Glove/Sock Formulation

| Trade Name | INCI Name | Weight (%) | Weight (g) |
|---|---|---|---|
| NA | Water | 71.9 | 359.5 |
| Versene NA2 (Dow Chemical (Joliet, Illinois)) | Disodium EDTA | 0.1 | 0.5 |
| Betafin BP-20 | Betaine | 2.0 | 10 |
| NA | D,L Panthenol | 0.5 | 2.5 |
| NA | Glycerin | 2.0 | 10 |
| NA | 1,3 Butylene glycol | 3.0 | 15 |
| Cosmedia SP | Sodium Polyacrylate | 0.8 | 4.0 |
| Emulgade CM | Ceteary isononanoate, Ceteareth-20, Cetearyl alcohol, Glyceryl | 15 | 75 |

TABLE 1B-continued

Global Glove/Sock Formulation

| Trade Name | INCI Name | Weight (%) | Weight (g) |
|---|---|---|---|
| Paragon MEPB | stearate, Glycerin, Ceteareth-12, Cetyl palmitate, Water Phenosyethanol, Methylparaben, Butylparaben, Ethylparaben, Propylparaben | 1.2 | 6.0 |
| Tinoderm A | Retinyl Palmitate, Caprylic/Capric Triglyceride, Polysorbate 80, Lecithin, WAter | 0.5 | 2.5 |
| Tinoderm E | Tocopheryl Acetate, Caprylic/Capric Triglyceride, Polysorbate 80, Lecithin, Water | 0.5 | 2.5 |
| Actiphyte of Aloe Vera extract 10 fold BG50P | Butylene Glycol, Water, Phenoxyethanol, Methylparaben, Ethylparaben, Propylparaben, Butylparaben, Isobutylparaben, Aloe Barbadensis, Leaf extract | 0.5 | 2.5 |
| Actiphyte of Avocado fold BG50P | utylene Glycol, Water, Phenoxyethanol, Methylparaben, Ethylparaben, Propylparaben, Butylparaben, Isobutylparaben, Persea Gratissima (avocado) fruit extract | 0.25 | 1.25 |
| Actiphyte of Jojoba Meal fold BG50P | Butylene Glycol, Water, Phenoxyethanol, Methylparaben, | 0.25 | 1.25 |
| Madarin & Ginger Flower 178470B | Ethylparaben, Propylparaben, Butylparaben, Isobutylparaben, Simmondsia Chinensis (jojoba) seed extract Fragrance | 1.5 | 7.5 |
| Total | | 100 | 500 |

To prepare the Global glove/sock formulation, water is added to Betafin BP20 and Panthenol and mixed until uniform. In a separate container, glycerin, butylene glycol, and Cosmedia SP were mixed until uniform and then added to the Betafin BP20/Panthenol/Water mixture. Emulgade CM is then added and mixed. Then, in order, Paragon MEPB, Tinoderm A, Tinoderm E, Aloe Vera, Avocado, Jojoba Meal, and fragrance was added and mixed until uniform. The pH of the formulation was then adjusted to approximately 5.6 to 6.0, if necessary. The Global glove/sock formulation is further commercially available from Kimberly-Clark Worldwide, Inc. (Neenah, Wis.).

Specifically, each outer spunbond nonwoven substrate was coated with one of the formulations in an amount of 100% w/w. Load values (i.e., measured as the amount of force required to stretch the substrate) were determined using STM 5683 at 30% elongation for untreated laminated articles as well as for the treated samples following one week of aging as described above. Additional load values at 60% elongation were tested. The load values for each treated substrate (average of six trials per sample substrate and formulation) were compared to untreated and unaged substrates as well as substrates having 100% w/w water added to the inner elastomeric film layer, aged as described above. The results are shown in Table 2.

TABLE 2

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 299.44 | 13.30 | NA | NA | 431.72 | 10.66 | NA | NA |
| Water-treated Substrate | 78.40 | 187.26 | 13.17 | 62.54 | NA | 323.54 | 8.01 | 74.94 | NA |
| Water/Silicone Emulsion | 6.80 | 166.14 | 13.51 | 55.48 | 88.72 | 282.64 | 17.19 | 65.47 | 87.36 |
| Global Glove/Stock Formulation (Kimberly-Clark Worldwide, Inc. (Neenah, Wisconsin)) | 44.00 | 150.95 | 14.48 | 50.41 | 80.61 | 256.37 | 12.33 | 59.38 | 79.24 |
| Mineral Oil | 2.10 | 26.63 | 2.32 | 8.89 | 14.22 | 55.90 | 3.24 | 12.95 | 17.28 |
| Isodecyl Neopentanoate and Diisopropyl Sebacate and Lauryl Lactate | 4.50 | 48.75 | 2.52 | 16.28 | 26.03 | 90.05 | 4.53 | 20.86 | 27.83 |
| Buytl Octisalate | 5.50 | 26.13 | 2.22 | 8.73 | 13.95 | 55.17 | 3.71 | 12.78 | 17.05 |
| PEG-5 Methyl Ether | 13.10 | 166.87 | 5.91 | 55.73 | 89.11 | 246.47 | 6.03 | 57.09 | 76.18 |

TABLE 2-continued

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Propylene Glycol | 32.00 | 237.57 | NA | 79.34 | 126.87 | 359.27 | NA | 83.22 | 111.04 |
| PEG-8 Dimethicone | 6.70 | 186.10 | 9.98 | 62.15 | 99.38 | 293.00 | 9.10 | 67.87 | 90.56 |
| Dimethicone 100 cst | 2.65 | 181.57 | 24.85 | 60.64 | 96.96 | 298.50 | 31.77 | 69.14 | 92.26 |
| PPG-3 Benzyl Ether Myristate | 4.50 | 134.20 | 5.52 | 44.82 | 71.67 | 221.00 | 5.99 | 51.19 | 68.31 |
| Lauryl Lactate | 5.51 | 100.58 | 4.12 | 33.59 | 53.71 | 159.68 | 6.91 | 36.99 | 49.36 |

As shown in Table 2, the samples coated with the water/silicone emulsion and the dimethicone (100 cst) had load retention values which were greater than the Global sock/glove formulation and consistently were among the more compatible materials tested.

Example 2

In this Example, various formulations were applied to a vertical filament laminated substrate. The degree of compatibility of the formulations and article were then determined.

The laminated article sample (112 gsm) was made by laminating elastomeric filaments extruded from molten elastomeric polymer pellets (commercially available as Triblock (Kraton® MD6688) from Kraton Polymers, LLC (Houston, Tex.)) between two polypropylene spunbond substrate layers, 14 gsm each. The layers were adhesively bonded using 2.5 grams/meter$^2$ of a rubber based hot melt adhesive (available as H2808-07 from Bostik Incorporated, Wauwatosa, Wis.).

The various formulations shown in Table 3 were applied to the article samples using the method of Example 1.

TABLE 3

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 56.98 | 3.38 | NA | NA | 88.84 | 3.62 | NA | NA |
| Water-treated Substrate | 78.40 | 55.90 | 3.96 | 98.10 | NA | 83.54 | 5.47 | 94.03 | NA |
| Water/Silicone Emulsion | 6.80 | 50.76 | 2.61 | 89.08 | 90.81 | 78.26 | 3.75 | 88.09 | 93.68 |
| Global Glove/Stock Formulation (Kimberly-Clark Worldwide, Inc. (Neenah, Wisconsin)) | 44.00 | 39.48 | 2.19 | 69.28 | 70.62 | 63.90 | 2.50 | 71.93 | 76.49 |
| Mineral Oil | 2.10 | 6.40 | 0.47 | 11.23 | 11.45 | 15.73 | 1.23 | 17.70 | 18.82 |
| Isodecyl Neopentanoate and Diisopropyl Sebacate and Lauryl Lactate | 4.50 | 4.33 | 0.42 | 7.59 | 7.74 | 10.60 | 2.18 | 11.93 | 12.69 |
| Buytl Octisalate | 5.50 | 4.05 | 0.58 | 7.11 | 7.25 | 7.88 | 1.15 | 8.86 | 9.43 |
| PEG-5 Methyl Ether | 13.10 | 49.78 | 2.88 | 87.36 | 89.04 | 74.68 | 3.55 | 84.06 | 89.39 |
| Propylene Glycol | 32.00 | 48.30 | 1.10 | 84.77 | 86.40 | 71.33 | 2.10 | 80.28 | 85.38 |
| PEG-8 Dimethicone | 6.70 | 24.15 | 4.22 | 42.38 | 43.20 | 30.35 | 7.58 | 34.16 | 36.33 |
| Dimethicone 100 cst | 2.65 | 56.15 | 3.00 | 98.54 | 100.45 | 83.95 | 4.18 | 94.50 | 100.49 |
| PPG-3 Benzyl Ether Myristate | 4.50 | 3.45 | 0.70 | 6.05 | 6.17 | 6.65 | 0.86 | 7.49 | 7.96 |
| Lauryl Lactate | 5.51 | 5.25 | 1.40 | 9.21 | 9.39 | 12.98 | 1.66 | 14.60 | 15.53 |

Example 3

In this Example, various formulations were applied to a 155 gsm elastomeric waistband material. The degree of compatibility of the formulations and article were then determined.

The elastomeric waistband material was made by laminating an elastomeric composite between two polypropylene spunbond layers of 14 gsm each. The elastomeric composite comprised elastomeric filaments extruded from molten elastomeric polymer pellets (commercially available as KRATON® MD6673 from Kraton Polymers, LLC of Houston, Tex.) and an elastomeric web of meltblown fibers extruded from molten elastomeric polymer pellets (commercially available as KC8020 from Bayshore Industrial of La Porte, Tex.), a blend of 80% AFFINITY EG8185 (Dow Chemical) and 20% REGALREZ 1126 (Eastman Chemical).

The various formulations shown in Table 4 were applied to the article samples using the method of Example 1.

TABLE 4

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 287.20 | 34.52 | NA | NA | 455.30 | 27.75 | NA | NA |
| Water-treated Substrate | 78.40 | 277.08 | 9.20 | 96.47 | NA | 424.45 | 13.41 | 93.22 | NA |
| Water/Silicone Emulsion | 6.80 | 222.60 | 9.73 | 77.51 | 80.34 | 352.88 | 13.33 | 77.50 | 83.14 |
| Global Glove/Stock Formulation (Kimberly-Clark Worldwide, Inc. (Neenah, Wisconsin)) | 44.00 | 208.13 | 8.12 | 72.47 | 75.12 | 335.55 | 8.26 | 73.70 | 79.06 |
| Mineral Oil | 2.10 | 71.08 | 1.72 | 24.75 | 25.65 | 128.85 | 4.75 | 28.30 | 30.36 |
| Isodecyl Neopentanoate and Diisopropyl Sebacate and Lauryl Lactate | 3.10 | 49.68 | 5.04 | 17.30 | 17.93 | 106.40 | 7.02 | 23.37 | 25.07 |
| Buytl Octisalate | 5.50 | 58.05 | 7.28 | 20.21 | 20.95 | 125.98 | 17.25 | 27.67 | 29.68 |
| PEG-5 Methyl Ether | 13.10 | 249.63 | 12.64 | 86.92 | 90.09 | 381.48 | 19.34 | 83.79 | 89.88 |
| Propylene Glycol | 32.00 | 259.93 | 12.33 | 90.50 | 93.81 | 392.83 | 12.86 | 86.28 | 92.55 |
| PEG-8 Dimethicone | 6.70 | 233.08 | 36.06 | 81.15 | 84.12 | 353.68 | 48.32 | 77.68 | 83.33 |
| Dimethicone 100 cst | 2.65 | 242.35 | 15.94 | 84.38 | 87.47 | 369.65 | 18.91 | 81.19 | 87.09 |
| PPG-3 Benzyl Ether Myristate | 4.50 | 73.33 | 13.18 | 25.53 | 26.46 | 150.23 | 23.80 | 32.99 | 35.39 |
| Lauryl Lactate | 5.51 | 92.90 | 17.97 | 32.35 | 33.53 | 144.73 | 35.78 | 31.79 | 34.10 |

Example 4

In this Example, various formulations were applied to a vertical filament laminated substrate having spunbond facings made from SFT-315 polymer pellets (commercially available from ExxonMobil, Houston, Tex.), which contain polypropylene with proprietary additives to enhance softness. The degree of compatibility of the formulations and article were then determined.

The laminated article sample (98 gsm) was made by laminating elastomeric filaments extruded from molten elastomeric polymer pellets (commercially available as KRATON® MD6688 from Kraton Polymers, LLC of Houston, Tex.) between two of the SFT-315 facing layers of 17 gsm each. The layers were adhesively bonded using 2.5 grams/meter2 of a rubber based hot melt adhesive (available as H2808-07 from Bostik Incorporated of Wauwatosa, Wis.).

The various formulations shown in Table 5 were applied to the laminated samples using the method of Example 1.

TABLE 5

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 65.74 | 5.59 | NA | NA | 95.86 | 7.86 | NA | NA |
| Water-treated Substrate | 78.40 | 71.33 | 7.98 | 108.50 | NA | 98.95 | 8.76 | 103.22 | NA |
| Water/Silicone Emulsion | 6.80 | 48.65 | 2.26 | 74.00 | 68.21 | 74.03 | 2.08 | 77.22 | 74.81 |
| Global Glove/Stock Formulation (Kimberly-Clark Worldwide, Inc., Neenah, Wisconsin) | 44.00 | 47.20 | 2.87 | 71.80 | 66.18 | 67.38 | 3.89 | 70.28 | 68.09 |
| Mineral Oil | 2.10 | 11.03 | 2.02 | 16.77 | 15.46 | 18.60 | 1.40 | 19.40 | 18.80 |
| Isodecyl Neopentanoate and Diisopropyl Sebacate and Lauryl Lactate | 4.50 | 4.28 | 0.43 | 6.50 | 5.99 | 21.30 | 18.01 | 22.22 | 21.53 |
| Buytl Octisalate | 5.50 | 4.98 | 0.88 | 7.57 | 6.98 | 18.38 | 8.54 | 19.17 | 18.57 |
| PEG-5 Methyl Ether | 13.10 | 28.18 | 3.19 | 42.86 | 39.50 | 38.15 | 1.82 | 39.80 | 38.55 |
| Propylene Glycol | 32.00 | 65.83 | 7.42 | 100.13 | 92.29 | 89.33 | 8.51 | 93.18 | 90.27 |
| PEG-8 Dimethicone | 6.70 | 23.28 | 1.38 | 35.40 | 32.63 | 26.08 | 3.45 | 27.20 | 26.35 |
| Dimethicone 100 cst | 2.65 | 58.80 | 4.82 | 89.44 | 82.44 | 84.28 | 7.10 | 87.91 | 85.17 |
| PPG-3 Benzyl Ether Myristate | 4.50 | 4.98 | 0.39 | 7.57 | 6.98 | 10.85 | 1.57 | 11.32 | 10.97 |
| Lauryl Lactate | 5.51 | 5.53 | 0.39 | 8.40 | 7.75 | 10.45 | 0.59 | 10.90 | 10.56 |

Example 5

In this Example, various formulations were applied to a 50 gsm elastomeric waistband material. The degree of compatibility of the formulations and article were then determined.

The elastomeric waistband material was made by laminating an elastomeric composite between two green spunbond layers of 14 gsm each, made from ACHIEVE™ 3155 polypropylene pellets (available from ExxonMobil, Houston, Tex.) dry-mixed with pellets of SCC-30104 green pigment concentrate (available from Standridge Color Corporation, Social Circle, Ga.). The elastomeric composite comprised elastomeric filaments extruded from molten elastomeric polymer pellets (commercially available as KRATON™ MD6673 from Kraton Polymers, LLC of Houston, Tex.) and an elastomeric web of meltblown fibers extruded from molten elastomeric polymer pellets (commercially available as KRATON™ KG2812 from Kraton Polymers, LLC of Houston, Tex.

The various formulations shown in Table 6 were applied to the laminated samples using the method of Example 1.

TABLE 6

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 107.48 | 9.27 | NA | NA | 170.84 | 14.53 | NA | NA |
| Water-treated Substrate | 78.40 | 86.88 | 6.25 | 80.83 | NA | 125.00 | 6.03 | 73.17 | NA |
| Water/Silicone Emulsion | 6.80 | 61.77 | 15.50 | 57.47 | 71.10 | 85.80 | 13.44 | 50.22 | 68.64 |
| Global Glove/Stock Formulation (Kimberly-Clark Worldwide, Inc., Neenah, Wisconsin) | 44.00 | 55.02 | 13.95 | 51.19 | 63.33 | 77.38 | 16.90 | 45.30 | 61.91 |

TABLE 6-continued

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Mineral Oil | 2.10 | | | | Delaminated | | | | |
| Isodecyl Neopentanoate and Diisopropyl Sebacate and Lauryl Lactate | 3.10 | | | | Delaminated | | | | |
| Buytl Octisalate | 5.50 | | | | Delaminated | | | | |
| PEG-5 Methyl Ether | 13.10 | 0.58 | 0.14 | 0.54 | 0.67 | 4.70 | 1.07 | 2.75 | 3.76 |
| Propylene Glycol | 32.00 | 78.68 | 2.40 | 73.21 | 90.57 | 109.23 | 3.77 | 63.94 | 87.39 |
| PEG-8 Dimethicone | 6.70 | 16.87 | 3.22 | 15.69 | 19.41 | 42.30 | 27.20 | 24.76 | 33.84 |
| Dimethicone 100 cst | 2.65 | 35.57 | 3.98 | 33.09 | 40.94 | 44.07 | 11.45 | 25.79 | 35.25 |
| PPG-3 Benzyl Ether Myristate | 4.50 | | | | Delaminated | | | | |
| Lauryl Lactate | 5.51 | NA | NA | NA | NA | NA | NA | NA | NA |

As shown in Table 6, visual inspection of the sample substrates coated with mineral oil, isopropyl palmitate, butyl octisalate, and PPG-3 benzyl ether myristate showed the substrate's structure was completely lost as the laminated layers had become undone. The waste band was 2 to 3 times its original length and had no extensibility.

Example 6

In this Example, various formulations were applied to a 90 gsm elastomeric waistband material. The degree of compatibility of the formulations and article were then determined.

The elastomeric waistband material was made by laminating an elastomeric composite between two blue spunbond layers of 14 gsm each, made from ACHIEVE™ 3155 polypropylene pellets (available from ExxonMobil, Houston, Tex.) dry-mixed with pellets of SCC-11111 blue pigment concentrate (available from Standridge Color Corporation, Social Circle, Ga.). The elastomeric composite comprised elastomeric filaments extruded from molten elastomeric polymer pellets (commercially available as KRATON™ MD6673 from Kraton Polymers, LLC of Houston, Tex.) and an elastomeric web of meltblown fibers extruded from molten elastomeric polymer pellets (commercially available as KRATON™ KG2812 from Kraton Polymers, LLC of Houston, Tex.

The various formulations shown in Table 7 were applied to the laminated samples using the method of Example 1.

TABLE 7

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 154.56 | 22.86 | NA | NA | 238.86 | 21.40 | NA | NA |
| Water-treated Substrate | 78.40 | 176.80 | 5.13 | 114.39 | NA | 251.40 | 4.41 | 105.25 | NA |
| Water/Silicone Emulsion | 6.80 | 148.50 | 4.42 | 96.08 | 83.99 | 215.55 | 7.72 | 90.24 | 85.74 |

Example 7

In this Example, various formulations were applied to the surface of a vertical filament laminated substrate made with spunbond facings having sheath/core fibers containing 50% each (by volume) of 3155 polypropylene (ExxonMobil, Houston, Tex.) and XUS-61800.41 polyethylene resin (Dow Chemical Company, Midland, Mich.) The degree of compatibility of the formulations and article were then determined.

The laminated substrate was made by laminating filaments extruded from molten elastomeric polymer pellets (commercially available as KRATON® MD6688 from Kraton Polymers, LLC of Houston, Tex.) between two of the spunbond facing layers of 14 gsm each. The layers were adhesively bonded using 2.5 grams/meter$^2$ of a rubber based hot melt adhesive (available as H2808-07 from Bostik, Incorporated of Wauwatosa, Wis.).

The various formulations shown in Table 8 were applied to the samples using the method of Example 1.

TABLE 8

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 103.02 | 9.09 | NA | NA | 150.34 | 11.65 | NA | NA |
| Water-treated Substrate | 78.40 | 108.70 | 6.09 | 105.51 | NA | 149.75 | 7.85 | 99.61 | NA |
| Water/Silicone Emulsion | 6.80 | 93.72 | 8.99 | 90.97 | 86.22 | 132.30 | 11.46 | 88.00 | 88.35 |
| Global Glove/Stock Formulation (Kimberly-Clark Worldwide, Inc., Neenah, Wisconsin) | 44.00 | 72.98 | 4.73 | 70.84 | 67.13 | 105.90 | 5.32 | 70.44 | 70.72 |
| Mineral Oil | 2.10 | | | | Delaminated | | | | |
| Isodecyl Neopentanoate and Diisopropyl Sebacate and Lauryl Lactate | 4.50 | | | | Delaminated | | | | |
| Buytl Octisalate | 5.50 | | | | Delaminated | | | | |
| PEG-5 Methyl Ether | 13.10 | 64.03 | 2.26 | 62.15 | 58.90 | 93.85 | 9.59 | 62.43 | 62.67 |
| Propylene Glycol | 32.00 | 81.68 | 4.37 | 79.28 | 75.14 | 120.50 | 4.79 | 80.15 | 80.47 |
| PEG-8 Dimethicone | 6.70 | 39.10 | 4.23 | 37.95 | 35.97 | 48.40 | 4.43 | 32.19 | 32.32 |
| Dimethicone 100 cst | 2.65 | 95.85 | 1.22 | 93.04 | 88.18 | 137.48 | 3.58 | 91.44 | 91.80 |
| PPG-3 Benzyl Ether Myristate | 4.50 | 5.93 | 1.58 | 5.75 | 5.45 | 16.45 | 5.17 | 10.94 | 10.98 |
| Lauryl Lactate | 5.51 | 5.05 | 1.35 | 4.90 | 4.65 | 16.85 | 3.82 | 11.21 | 11.25 |

As shown in Table 8, visual inspection of the sample substrates coated with mineral oil, isopropyl palmitate, butyl octisalate, and PPG benzyl ether myristate showed the substrate's structure was completely lost as the laminated layers had become undone. The substrate was 2 to 3 times its original length and had no extensibility.

Example 8

In this Example, various formulations were applied to the surface of a vertical filament laminated substrate made with 17 gsm polyethylene spunbond facing from BBA Fiberweb (London, U.K.). The degree of compatibility of the formulations and article were then determined.

The laminated substrate was made by laminating filaments extruded from molten elastomeric polymer pellets (commercially available as KRATON® MD6688 from Kraton Polymers, LLC of Houston, Tex.) between two of the spunbond facing layers. The layers were adhesively bonded using 2.5 grams/meter$^2$ of a rubber based hot melt adhesive (available as H2808-07 from Bostik, Incorporated of Wauwatosa, Wis.).

The various formulations shown in Table 9 were applied to the laminated samples using the method of Example 1.

TABLE 9

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 97.18 | 5.30 | NA | NA | 147.84 | 7.55 | NA | NA |
| Water-treated Substrate | 78.40 | 96.62 | 10.86 | 99.42 | NA | 136.56 | 12.65 | 92.37 | NA |
| Water/Silicone Emulsion | 6.80 | 88.30 | 8.06 | 90.86 | 91.39 | 126.26 | 11.90 | 85.40 | 92.46 |
| Global Glove/Stock Formulation (Kimberly-Clark Worldwide, Inc., Neenah, Wisconsin) | 44.00 | 61.90 | 4.83 | 63.70 | 64.07 | 96.60 | 5.37 | 65.34 | 70.74 |

TABLE 9-continued

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Mineral Oil | 2.10 | 16.10 | 1.29 | 16.57 | 16.66 | 22.63 | 0.78 | 15.30 | 16.57 |
| Isodecyl Neopentanoate and Diisopropyl Sebacate and Lauryl Lactate | | | | | Delamination | | | | |
| Buytl Octisalate | | | | | Delamination | | | | |
| PEG-5 Methyl Ether | 13.10 | 86.28 | 5.72 | 88.78 | 89.29 | 127.00 | 9.11 | 85.90 | 93.00 |
| Propylene Glycol | 32.00 | 94.65 | 7.64 | 97.40 | 97.96 | 135.58 | 7.62 | 91.70 | 99.28 |
| PEG-8 Dimethicone | 6.70 | 87.65 | 7.97 | 90.19 | 90.72 | 129.40 | 10.42 | 87.53 | 94.76 |
| Dimethicone 100 cst | 2.65 | 104.35 | 9.14 | 107.38 | 108.00 | 144.53 | 8.91 | 97.76 | 105.83 |
| PPG-3 Benzyl Ether Myristate | | | | | Delamination | | | | |
| Lauryl Lactate | | | | | Delamination | | | | |

As shown in Table 9, visual inspection of the sample substrates coated with mineral oil, isopropyl palmitate, butyl octisalate, PPG benzyl ether myristate, and lauryl lactate showed the substrate's structure was completely lost as the laminated layers had become undone. The substrate sample was 2 to 3 times its original length and had no extensibility.

Example 9

In this Example, various formulations were applied to the surface of an apertured elastomeric film laminate. The degree of compatibility of the formulations and film were then determined.

The film layers of the laminate were made using 35 gsm of VISTAMAXX™ 1100 (ExxonMobil, Houston, Tex.) blended with 2% (by weight) SCC-4837 titanium dioxide pigment concentrate, available from Standridge Color Corporation (Social Circle, Ga.). The film layers were then stretched at a draw ratio of 3.5 (350% elongation) and laminated between two 18 gsm stretch-bonded facings made from SFT-315 polymer pellets (commercially available from ExxonMobil, Houston, Tex.), which contain polypropylene with proprietary additives to enhance softness. Lamination and aperturing were accomplished simultaneously using a thermal point bonding process using a rotary bonder with a patterned bonding roll. The film laminate produced was approximately 130 to 140 gsm.

The various formulations shown in Table 10 were applied to the laminated samples using the method of Example 1.

TABLE 10

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 170.20 | 9.73 | NA | NA | 273.98 | 16.88 | NA | NA |
| Water-treated Substrate | 78.40 | 222.98 | 73.89 | 131.01 | NA | 327.92 | 85.98 | 119.69 | NA |
| Water/Silicone Emulsion | 6.80 | 142.72 | 19.19 | 83.85 | 64.01 | 225.62 | 26.46 | 82.35 | 68.80 |
| Global Glove/Stock Formulation (Kimberly-Clark Worldwide, Inc., Neenah, Wisconsin) | 44.00 | 114.93 | 6.53 | 67.52 | 51.54 | 197.78 | 10.33 | 72.19 | 60.31 |
| Mineral Oil | 2.10 | 19.83 | 4.63 | 11.65 | 8.89 | 49.55 | 6.91 | 18.09 | 15.11 |
| Isodecyl Neopentanoate and Diisopropyl Sebacate and Lauryl Lactate | 4.50 | 33.80 | 6.14 | 19.86 | 15.16 | 70.08 | 10.22 | 25.58 | 21.37 |

TABLE 10-continued

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Buytl Octisalate | 5.50 | 26.80 | 7.34 | 15.75 | 12.02 | 59.65 | 10.96 | 21.77 | 18.19 |
| PEG-5 Methyl Ether | 13.10 | 142.83 | 25.25 | 83.92 | 64.05 | 229.93 | 33.03 | 83.92 | 70.12 |
| Propylene Glycol | 32.00 | 140.33 | 9.11 | 82.45 | 62.93 | 229.95 | 9.52 | 83.93 | 70.12 |
| PEG-8 Dimethicone | 6.70 | 127.13 | 8.08 | 74.69 | 57.01 | 211.93 | 7.94 | 77.35 | 64.63 |
| Dimethicone 100 cst | 2.65 | 144.10 | 8.02 | 84.67 | 64.62 | 224.13 | 11.35 | 81.80 | 68.35 |
| PPG-3 Benzyl Ether Myristate | 4.50 | 99.65 | 3.17 | 58.55 | 44.69 | 168.73 | 4.88 | 61.58 | 51.45 |
| Lauryl Lactate | 5.51 | 79.55 | 23.23 | 46.74 | 35.68 | 134.45 | 36.61 | 49.07 | 41.00 |

Overall, many substrates coated with the various formulations of the present disclosure retained 40% or more of the untreated substrate at 30% elongation, with a majority of these substrates retaining at least 70-80% or more of the untreated substrate at 30% elongation.

Example 10

In this Example, various formulations were applied to the facings of an experimental laminate. The degree of compatibility of the formulations and laminate were then determined.

The experimental laminate of this example was made using a multilayer film having a "skin-core" structure, laminated between polypropylene spunbond facing layers. The core of the multilayer film component comprised 94 weight % of the film and the skin layers on each side of the core comprised 6 weight % of the film. The core was formed from 75% of KRATON™ MD6673 (Kraton Polymers, LLC of Houston Tex.) and 25% of EXACT™ 5361 (ExxonMobil Chemical Co.) by weight. The skin composition comprised a blend of 50% CATALLOY™ KS527 (LyondellBassell, Brussels, Belgium) and 50% VISTAMAXX™ 1100 (ExxonMobil, Houston, Tex.).

The multilayer film components were compounded by weighing appropriate portions of pellets of each polymer, combining them into one container, and mixing them together by stirring. After compounding, the film components were extruded using a small scale triple screw blown film line with a 1.75-inch extruder (Killion) and two 16-millimeter extruders (Collin GmbH). The blown film line also employed an air ring (Collin GmbH), 3-inch die (Collin GmbH), and collapsing tower (Killion). Each extruder had three temperature zones and a die with a controlled temperature. The core layer was extruded from the 1.75-inch extruder and one of the 16-mm extruders, and the skin layer was extruded from the second 16-mm extruder. The temperature profile for the core extruders was arranged so that a melt temperature of about 375° F. was achieved. The temperature profile for the skin extruder was arranged so that a melt temperature of about 190° C. was achieved.

After quenching from the air ring and collapsing the bubble (collapsing nip was run at 20 feet per minute), the film was stretched in the machine direction at a draw ratio of 3 (i.e., 3 times its original length). The film was stretched between two sets of driven nips. The first nip ran at 20 feet per minute, and the second nip ran at 60 feet per minute to provide the draw ratio of 3. The film was then laminated in the stretched state between two polypropylene spunbond facing layers, each having a basis weight of approximately 13.6 grams per square meter. Lamination was accomplished by a thermal point bonding process using a rotary bonder with a square diamond bond pattern having a bond area of 8%-14% and a pin density of 52 pins per square inch. Anvil and patterned rolls were employed at 230° F. and a pressure of 40 pounds per square inch on both sides of the rotary bonder. The various formulations shown in Table 11 were applied to the laminated samples using the method of Example 1.

TABLE 11

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 282.36 | 28.22 | NA | NA | 477.56 | 33.32 | NA | NA |
| Water-treated Substrate | 78.40 | 307.24 | 31.22 | 108.81 | NA | 496.72 | 44.67 | 104.01 | NA |
| Water/Silicone Emulsion | 6.80 | 288.80 | 29.72 | 102.28 | 94.00 | 470.64 | 39.60 | 98.55 | 94.75 |

TABLE 11-continued

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Global Glove/Stock Formulation (Kimberly-Clark Worldwide, Inc., Neenah, Wisconsin) | 44.00 | 232.20 | 10.36 | 82.24 | 75.58 | 408.85 | 4.12 | 85.61 | 82.31 |
| Mineral Oil | 2.10 | 56.08 | 13.59 | 19.86 | 18.25 | 124.85 | 21.39 | 26.14 | 25.13 |
| Isodecyl Neopentanoate and Diisopropyl Sebacate and Lauryl Lactate | 4.50 | 51.25 | 9.75 | 18.15 | 16.68 | 99.60 | 16.28 | 20.86 | 20.05 |
| Buytl Octisalate | 5.50 | 37.05 | 2.87 | 13.12 | 12.06 | 75.23 | 2.65 | 15.75 | 15.14 |
| PEG-5 Methyl Ether | 13.10 | 258.03 | 24.13 | 91.38 | 83.98 | 419.38 | 29.68 | 87.82 | 84.43 |
| Propylene Glycol | 32.00 | 269.68 | 7.97 | 95.51 | 87.77 | 445.00 | 12.53 | 93.18 | 89.59 |
| PEG-8 Dimethicone | 6.70 | 215.70 | 45.66 | 76.39 | 70.21 | 412.63 | 24.09 | 86.40 | 83.07 |
| Dimethicone 100 cst | 2.65 | 297.43 | 20.41 | 105.34 | 96.81 | 491.63 | 27.81 | 102.95 | 98.97 |
| PPG-3 Benzyl Ether Myristate | 4.50 | 109.38 | 12.21 | 38.74 | 35.60 | 193.95 | 13.64 | 40.61 | 39.05 |
| Lauryl Lactate | 5.51 | 134.08 | 23.06 | 47.48 | 43.64 | 266.05 | 17.07 | 55.71 | 53.56 |

Example 11

In this Example, various formulations were applied to the facings of an experimental laminate. The degree of compatibility of the formulations and laminates were then determined.

As in previous Example 10, the experimental laminate of this example was made using a multilayer film having a "skin-core" structure, laminated between polypropylene spunbond facing layers. The core of the multilayer film component comprised 94 weight % of the film and the skin layers on each side of the core comprised 6 weight % of the film. The core was formed from 75% of KRATON™ MD6673 (Kraton Polymers, LLC, Houston Tex.) and 25% of EXACT™ 5361 (ExxonMobil, Houston, Tex.) by weight. The skin composition comprised a blend of 40% SCC 22181, a filler compound, which contained calcium carbonate blended with polypropylene and polypropylene random copolymers (Standridge Color Corporation, Social Circle, Ga.) and 60% VISTAMAXX™ 1100 (ExxonMobil, Houston, Tex.). The multilayer films were made by coextrusion of the different layers through a die consisting of concentric rings, as described in Example 10. The multilayer films were then laminated to outer spunbond layers by thermal pattern bonding at a temperature of 230° F. (110° C.) and a pressure of approximately 40 psi.

The various formulations shown in Table 12 were applied to the laminated samples using the method of Example 1.

TABLE 12

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 191.54 | 55.67 | NA | NA | 403.34 | 49.62 | NA | NA |
| Water-treated Substrate | NA | 270.68 | 31.18 | 141.32 | NA | 443.33 | 28.92 | 109.91 | NA |
| Water/Silicone Emulsion | 78.40 | 239.25 | 19.72 | 124.91 | 88.39 | 400.10 | 22.29 | 99.20 | 90.25 |
| Global Glove/Stock Formulation (Kimberly-Clark Worldwide, Inc., Neenah, Wisconsin) | 44.00 | 243.95 | 22.53 | 127.36 | 90.13 | 395.90 | 41.25 | 98.16 | 89.30 |

TABLE 12-continued

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Mineral Oil | 2.10 | 80.90 | 21.48 | 42.24 | 29.89 | 182.88 | 28.35 | 45.34 | 41.25 |
| Isodecyl Neopentanoate and Diisopropyl Sebacate and Lauryl Lactate | 4.50 | 52.43 | 10.12 | 27.37 | 19.37 | 90.03 | 16.70 | 22.32 | 20.31 |
| Buytl Octisalate | 5.50 | 40.38 | 3.56 | 21.08 | 14.92 | 77.33 | 7.19 | 19.17 | 17.44 |
| PEG-5 Methyl Ether | 13.10 | 241.78 | 28.62 | 126.23 | 89.32 | 426.75 | 27.07 | 105.80 | 96.26 |
| Propylene Glycol | 32.00 | 288.53 | 34.29 | 150.64 | 106.60 | 449.00 | 36.38 | 111.32 | 101.28 |
| PEG-8 Dimethicone | 6.70 | 280.48 | 14.00 | 146.43 | 103.62 | 437.30 | 25.59 | 108.42 | 98.64 |
| Dimethicone 100 cst | 2.65 | 286.25 | 29.52 | 149.45 | 105.75 | 457.43 | 39.97 | 113.41 | 103.18 |
| PPG-3 Benzyl Ether Myristate | 4.50 | 97.98 | 18.04 | 51.15 | 36.20 | 177.53 | 19.71 | 44.01 | 40.04 |
| Lauryl Lactate | 5.51 | 163.83 | 9.19 | 85.53 | 60.52 | 248.68 | 17.41 | 61.65 | 56.09 |

Example 12

In this Example, various formulations were applied to the facings of an experimental laminate. The degree of compatibility of the formulations and laminate were then determined.

As in Example 10, the experimental laminate of this example was made using a multilayer film having a "skin-core" structure, laminated between polypropylene spunbond facing layers. The core of the multilayer film component comprised 94 weight % of the film and the skin layers on each side of the core comprised 6 weight % of the film. The core was formed from 75% of KRATON® MD6673 (Kraton Polymers, LLC, Houston Tex.) and 25% of EXACT™ 5361 (ExxonMobil, Houston, Tex.) by weight. The skin composition comprised a blend of 45% SCC 22181, a filler compound, which contained calcium carbonate blended with polypropylene and polypropylene random copolymers (Standridge Color Corporation, Social Circle, Ga.), 45% VISTAMAXX™ 1100 (ExxonMobil, Houston, Tex.), and 10% 04SAM0749, which contained REGALREZ™ hydrocarbon tackifier resin (Eastman Chemical, Kingsport, Tenn.) blended with polypropylene (Standridge Color Corporation). The multilayer films were made by coextrusion of the different layers through a die consisting of concentric rings, as described in Example 10. The multilayer films were then laminated to outer spunbond layers by thermal pattern bonding at a temperature of 230° F. (110° C.) and a pressure of approximately 40 psi.

The various formulations shown in Table 13 were applied to the laminated samples using the method of Example 1.

TABLE 13

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Uncoated Substrate | NA | 227.30 | 24.83 | NA | NA | 390.34 | 24.40 | NA | NA |
| Water-treated Substrate | 78.40 | NA | NA | 0.00 | NA | NA | NA | NA | NA |
| Water/Silicone Emulsion | 6.80 | NA | NA | 0.00 | NA | NA | NA | NA | NA |
| Global Glove/Stock Formulation (Kimberly-Clark Worldwide, Inc., Neenah, Wisconsin) | 44.00 | 230.78 | 10.11 | 101.53 | NA | 358.03 | 18.16 | 91.72 | NA |
| Mineral Oil | 2.10 | 45.58 | 8.76 | 20.05 | NA | 102.13 | 8.73 | 26.16 | NA |
| Isodecyl Neopentanoate and Diisopropyl Sebacate and Lauryl Lactate | 4.50 | 49.70 | 6.48 | 21.87 | NA | 85.18 | 7.52 | 21.82 | NA |

TABLE 13-continued

| Formulation | Dielectric Constant of Formulation | Load Value at 30% Elongation (gf/in) | Std. Dev. | Original Load Retained (%) | Load Retained from Water-treated substrates (%) | Load at 60% Elongation (gf/in) | Std. Dev. | Original Load Retained (%) | Load Retained from Water-treated substrates (%) |
|---|---|---|---|---|---|---|---|---|---|
| Buytl Octisalate | 5.50 | 36.60 | 7.00 | 16.10 | NA | 69.50 | 9.42 | 17.80 | NA |
| PEG-5 Methyl Ether | 13.10 | 250.43 | 23.54 | 110.17 | NA | 383.93 | 27.96 | 98.36 | NA |
| Propylene Glycol | 32.00 | 271.68 | 25.03 | 119.52 | NA | 406.40 | 35.54 | 104.11 | NA |
| PEG-8 Dimethicone | 6.70 | 271.50 | 28.79 | 119.45 | NA | 413.08 | 39.53 | 105.82 | NA |
| Dimethicone 100 cst | 2.65 | 204.15 | 8.84 | 89.82 | NA | 335.73 | 14.11 | 86.01 | NA |
| PPG-3 Benzyl Ether Myristate | 4.50 | 76.80 | 10.45 | 33.79 | NA | 132.95 | 8.09 | 34.06 | NA |
| Lauryl Lactate | 5.51 | 162.05 | 53.08 | 71.29 | NA | 269.65 | 48.29 | 69.08 | NA |

Example 13

In this Example, various formulations were applied to the facings of a laminated article. The degree of compatibility of the formulations and article were then determined.

The laminated samples were made using 27 strands of 800 dtex LYCRA® spandex, available from Invista (Wichita, Kans.), extended to 250% elongation and spaced approximately 3 mm apart. The samples were adhesively laminated between two soft facing layers. The 20-gsm spunbond facing layers were made from SFT-315 polymer pellets (commercially available from ExxonMobil, Houston, Tex.), which contain polypropylene with propriety additives to enhance softness. Specifically, 5 gsm of H20030 hot melt adhesive, available from Bostik Incorporated of Wauwatosa, Wis., was used to laminate the spandex strands to the facings.

The various formulations shown in Table 14 were applied to the laminated samples using the method of Example 1.

TABLE 14

| Solution | $\varepsilon_r$ | Load at 30% Elongation (gf/in) | Std Dev. | Original Load Retained (%) | Load Retained from Water Treated Samples (%) | Load at 60% Elongation (gf/in) | Std Dev. | Original Load Retained (%) | Load Retained from Water Sample (%) |
|---|---|---|---|---|---|---|---|---|---|
| Uncoated Basesheet | NA | 131.54 | 5.37 | NA | NA | 216.32 | 7.40 | NA | NA |
| Basesheet with Water | 78.40 | 129.55 | 3.86 | 98.49 | NA | 210.18 | 5.91 | 97.16 | NA |
| Water/Silicone Emulsion (K158-010) | 6.80 | 126.80 | 6.46 | 96.40 | 97.88 | 205.53 | 9.89 | 95.01 | 97.79 |
| Global Glove/Sock Formulation (Kimberly-Clark Worldwide, Inc., Neenah, Wisconsin) | 44.00 | 121.43 | 6.89 | 92.31 | 93.73 | 198.10 | 8.80 | 91.58 | 94.25 |
| Mineral Oil | 2.10 | | | Delaminated Lycra Strands from the Basesheet | | | | | |
| Dub Synersol | 4.50 | | | Delaminated Lycra Strands from the Basesheet | | | | | |
| Buytl Octisalate | 5.50 | | | Delaminated Lycra Strands from the Basesheet | | | | | |
| PEG-5 Methyl Ether | 13.10 | | | Delaminated Lycra Strands from the Basesheet | | | | | |
| Propylene Glycol | 32.00 | 107.58 | 4.71 | 81.78 | 83.04 | 181.30 | 2.23 | 83.81 | 86.26 |
| PEG-8 Dimethicone | 6.70 | | | Delaminated Lycra Strands from the Basesheet | | | | | |
| Dimethicone 100 cst | 2.65 | 132.53 | 4.25 | 100.75 | 102.30 | 213.68 | 6.59 | 98.78 | 101.67 |
| PPG-3 Benzyl Ether Myristate | 4.50 | | | Delaminated Lycra Strands from the Basesheet | | | | | |
| Lauryl Lactate | 5.51 | | | Delaminated Lycra Strands from the Basesheet | | | | | |

Example 14

In this Example, a water-in-silicone emulsion was applied to a polyester film. The degree of compatibility of the formulation and film were then determined and compared to an uncoated film.

The polyester film used was Polyester TPU 85 shore A, commercially available as Irogran PS79-200 from Huntsman Film Products Corporation (Salt Lake City, Utah).

The various formulations shown in Table 15 were applied to the film samples using the method of Example 1.

TABLE 15

| Formulation | Dielectric Constant of Formulation | Load Value at 30% Elongation (gf/in) | Std. Dev. | Original Load Retained (%) | Load at 60% Elongation (gf/in) | Std. Dev. | Original Load Retained (%) |
|---|---|---|---|---|---|---|---|
| Uncoated film | NA | 668.90 | 30.70 | NA | 854.60 | 47.10 | NA |
| Water/Silicone Emulsion | 6.80 | 536.60 | 26.20 | 80.22 | 726.70 | 37.80 | 85.03 |

Example 15

In this Example, a water-in-silicone emulsion was applied to a polyether film. The degree of compatibility of the formulation and film were then determined and compared to an uncoated film.

The polyether film used was Polyether TPU 85 shore A, commercially available as Irogran A85P4394 from Huntsman Film Products Corporation (Salt Lake City, Utah).

The various formulations shown in Table 16 were applied to the film samples using the method of Example 1.

TABLE 16

| Formulation | Dielectric Constant of Formulation | Load Value at 30% Elongation (gf/in) | Std. Dev. | Original Load Retained (%) | Load at 60% Elongation (gf/in) | Std. Dev. | Original Load Retained (%) |
|---|---|---|---|---|---|---|---|
| Uncoated film | NA | 624.60 | 12.70 | NA | 766.60 | 14.00 | NA |
| Water/Silicone Emulsion | 6.80 | 444.20 | 24.90 | 66.41 | 619.00 | 21.50 | 80.75 |

Example 16

In this Example, water/silicone emulsions having varied levels of mineral oil were applied to a Lycra substrate using the application methods as described in Example 1. The emulsions are shown in Table 17.

TABLE 17

| | | | Water/Silicone Emulsion | | | |
|---|---|---|---|---|---|---|
| Supplier | Tradename | INCI name | K158-042 emulsion Weight (%) | K158-043 emulsion Weight (%) | K158-044 emulsion Weight (%) | K158-045 emulsion Weight (%) |
| Phase A | | | | | | |
| NA | Water | Water | 35.1 | 35.1 | 35.1 | 35.1 |
| COGNIS Co. (Cincinnati, Ohio) | Elestab FL-15 | Butylene Glycol, Glycerin Methylparaben, Chlorophenesin | 2.0 | 2.0 | 2.0 | 2.0 |
| Mallinckrodt (St. Louis, Missouri) | NA | Magnesium Sulfate Heptahydrate | 0.8 | 0.8 | 0.8 | 0.8 |
| Rita (Washington DC) | NA | Propylene Glycol | 5.0 | 5.0 | 5.0 | 5.0 |
| Dow Chemical (Joliet, Illinois) | Versene NA2 | Disodium EDTA | 0.1 | 0.1 | 0.1 | 0.1 |
| Phase B | | | | | | |
| Dow Corning (Midland, Michigan) | DC 200 10 cst | Dimethicone | 25 | 15 | 35 | 0 |
| Penreco (Dickinson, Texas) | Drakeol 7 | Mineral Oil | 25 | 35 | 15 | 50 |

TABLE 17-continued

| | | | Water/Silicone Emulsion | | | |
|---|---|---|---|---|---|---|
| Supplier | Tradename | INCI name | K158-042 emulsion Weight (%) | K158-043 emulsion Weight (%) | K158-044 emulsion Weight (%) | K158-045 emulsion Weight (%) |
| Barnet (Herfordshire, UK) | NET-WO | Cyclopentasiloxane, PEG-10 Dimethicone, Distearyldimonium Hectorite | 7 | 7 | 0 | 0 |
| Barnet (Herfordshire, UK) | NET-WO NS | Polyglyceryl-6 Polyricnoleate, Polyglyceryl-2 Isostearate, Disteardimonium Hectorite | 0 | 0 | 7 | 7 |
| Total | | | 100 | 100 | 100 | 100 |

The emulsions were made by first heating the water to a temperature of about 50° C. The remaining ingredients of Phase A where then added to the water and mixed until uniform. NET-WO or NET-WO NS from Phase B were then dispersed into the DC 200 and/or mineral oil at 50° C. Phase A and Phase B were gradually homogenized (approximately 10-15 grams at a time) until the free liquid is incorporated into the emulsion. The emulsion was allowed to cool to room temperature and then homogenized again.

The degree of compatibility of the formulations and article were then determined and compared to an uncoated substrate. The results are shown in Table 18.

TABLE 18

| | | Lycra/Spandex | | | | | |
|---|---|---|---|---|---|---|---|
| Solution | $\varepsilon_r$ | Cosmetic Carriers in Oil Phase | Load at 30% Elongation (gf/in) | Std Dev. | Original Load Retained (%) | Load at 60% Elongation (gf/in) | Std Dev. | Original Load Retained (%) |
| Uncoated Basesheet | NA | NA | 131.54 | 13.30 | NA | 216.32 | 7.40 | NA |
| K158-010 | 6.80 | 50% Dimethicone; 0% Mineral Oil | 129.55 | 3.86 | 98.49 | 210.18 | 5.91 | 97.16 |
| K158-042 | 4.62 | 25% Dimethicone; 25% Mineral Oil | 111.68 | 3.35 | 84.90 | 176.03 | 7.76 | 81.37 |
| K158-043 | 4.27 | 35% Dimethicone; 15% Mineral Oil | 115.38 | 5.90 | 87.71 | 185.73 | 13.33 | 85.86 |
| K158-044 | 7.30 | 15% Dimethicone; 35% Mineral Oil | 104.78 | 3.13 | 79.65 | 170.50 | 8.70 | 78.82 |
| K158-045 | 8.15 | 0% Dimethicone; 50% Mineral Oil | 27.80 | 9.70 | 21.13 | 64.90 | 19.90 | 30.00 |

Example 17

In this Example, the effect of coating various amounts of mineral oil onto the laminated articles described in Example 1 was determined.

Specifically, coating of the laminated articles with mineral oil was conducted using a 2-ounce Boston Round spray bottle (available from Silgan Plastics, LLC, Stamford, Conn.) and the appropriate dispensing pump (available as Seaquist Perfect Dispensing Pump, Aptar Group, Co., Crystal Lake, Ill.). Samples were then aged for one week at 131° F. (55° C.) prior to testing. The results are shown in Table 19.

TABLE 19

| Solution | Load at 30% Elongation (gf/in) | Std Dev. | Original Load Retained (%) | Load at 60% Elongation (gf/in) | Std Dev. | Original Load Retained (%) |
|---|---|---|---|---|---|---|
| Uncoated Basesheet | 299.44 | 13.30 | 100.00 | 431.72 | 10.66 | 100.00 |
| 100% Mineral Oil | 26.63 | 2.32 | 8.89 | 55.90 | 3.24 | 12.95 |
| 25% Mineral Oil | 29.70 | 6.90 | 9.92 | 62.30 | 14.00 | 14.43 |
| 10% Mineral Oil | 42.90 | 16.20 | 14.33 | 77.20 | 25.50 | 17.88 |

As these findings indicate, formulations containing 10% or more mineral oil are likely to result in significant loss of load during elongation. Formulations in which the oil phase is comprised of greater than 70% by weight a cosmetic carrier or combination of cosmetic carriers which themselves retain the load values of the untreated substrate, such as dimethicone, is necessary for the present disclosure. The water soluble cosmetic carriers described within the specification of this application such as Propylene Glycol and PEG-8 Dimethicone can be used without limitation.

Example 18

In this Example, various oil-containing formulations were used on the laminated article of Example 1. The degree of compatibility of the oil-containing formulations on the substrate was determined.

Specifically, as noted above, within laminated articles, the integrity of the bonding which exists between two or more layers may be compromised by the presence of oil, resulting in the delamination of the entire article. The article of Example 1 was coated with 100% w/w of the oil-containing formulations shown in Table 20. The overall load retention (e.g., compatibility) of the formulation with the article was tested.

TABLE 20

| Formulation | Dielectric Constant ($\varepsilon_r$) | Peak Load | Standard Deviation | Original Load Retained (%) |
|---|---|---|---|---|
| Untreated substrate | NA | 195.33 | 23.35 | 100.00 |
| Global Glove/Sock Formulation | 44.00 | 241.50 | 73.74 | 123.63 |
| Water/Silicone Formulation (K158-010) | 6.80 | 115.60 | 11.87 | 59.10 |
| Mineral Oil | 2.13 | 31.00 | 3.58 | 15.87 |
| Isopropyl Palmitate | 3.2 | 32.00 | 3.10 | 16.38 |
| Octisalate | 6.2 | 44.33 | 6.89 | 22.70 |
| Cyclomethicone | 2.5 | 61.50 | 11.64 | 31.48 |
| PEG-5 Methyl Ether | 13.1 | 250.83 | 29.88 | 128.41 |
| Diethylexyl 2,6 napthalate | 4.34 | 211.17 | 77.80 | 108.11 |
| PEG-3 dimethicone | 4.8 | 168.67 | 53.84 | 86.35 |
| PEG-8 dimethicone | 6.7 | 177.50 | 51.34 | 90.87 |

As shown in Table 20, oil-containing formulations having similar polarities, resulted in significantly different overall retention of peak load.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above formulations and substrates/articles without departing from the scope of the disclosure, it is intended that all matter contained in the above description shall be interpreted as illustrative and not in a limiting sense.

What is claimed is:

1. An elastomeric substrate comprising a formulation comprising greater than 5% (by weight formulation) water, from about 25% to about 57% (by weight formulation) of at least one cosmetic carrier, wherein the at least one cosmetic carrier is dimethicone, and wherein the at least one cosmetic carrier comprises greater than 70% by weight of an oil phase of the formulation, wherein the formulation is a water-in-silicone emulsion, wherein the formulation has a dielectric constant of from about 6.0 to about 35.0, and wherein the elastomeric substrate retains at least about 80% of the tension of the untreated substrate at 30% elongation.

2. The elastomeric substrate as set forth in claim 1 wherein the substrate includes at least 10% w/w formulation.

3. The elastomeric substrate as set forth in claim 1 wherein the formulation comprises greater than about 10% (by weight formulation) water.

4. A nonwoven substrate comprising a formulation comprising greater than 5% (by weight formulation) water, from about 25% to about 57% (by weight formulation) of at least one cosmetic carrier, wherein the at least one cosmetic carrier is dimethicone, and wherein the at least one cosmetic carrier comprises greater than 70% by weight of an oil phase of the formulation, wherein the formulation is a water-in-silicone emulsion, wherein the formulation has a dielectric constant of from about 6.0 to about 35.0, and wherein the nonwoven substrate retains at least about 80% of the tension of the untreated substrate at 30% elongation.

5. The nonwoven substrate as set forth in claim 4 wherein the substrate includes at least 10% w/w formulation.

6. The nonwoven substrate as set forth in claim 4 wherein the formulation comprises greater than about 10% (by weight formulation) water.

7. A laminated article comprising:
a first substrate; and
a second substrate, wherein at least one of the first and second substrates comprises a formulation, the formulation comprising:
greater than 5% (by weight formulation) water,
from about 25% to about 57% (by weight formulation) of at least one cosmetic carrier, wherein the at least one cosmetic carrier is dimethicone, and wherein the at least one cosmetic carrier comprises greater than 70% by weight of an oil phase of the formulation, wherein the formulation is a water-in-silicone emulsion, wherein the formulation has a dielectric constant of from about 6.0 to about 35.0, and wherein the laminated article retains at least 80% of the tension of the untreated article at 30% elongation.

8. The laminated article as set forth in claim 7 wherein the article includes at least 10% w/w formulation.

9. The laminated article as set forth in claim 7 wherein the first substrate is a nonwoven substrate and the second substrate is a water-impermeable layer.

10. The laminated article as set forth in claim 7 wherein the formulation comprises from about 25% to about 35% (by weight formulation) of cosmetic carrier.

11. The laminated article as set forth in claim 7 wherein the formulation comprises less than 25% of mineral oil.

* * * * *